(12) United States Patent
Nikiforov

(10) Patent No.: US 6,287,774 B1
(45) Date of Patent: Sep. 11, 2001

(54) ASSAY METHODS AND SYSTEM

(75) Inventor: Theo T. Nikiforov, San Jose, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/316,447

(22) Filed: May 21, 1999

(51) Int. Cl.$^7$ .............................. C12Q 1/68; C12P 19/34; C12M 1/34; C07H 21/04; C25B 5/00

(52) U.S. Cl. ............................ 435/6; 435/91.1; 435/91.2; 435/258.1; 435/285.2; 435/287.1; 435/287.2; 436/171; 436/172; 536/22.1; 536/23.1; 536/24.3; 536/24.31; 536/24.32; 536/24.33; 204/155

(58) Field of Search .............................. 435/6, 7.1, 91.1, 435/91.2, 194, 183, 283.1, 285.1, 285.2, 287.1, 287.2; 436/164, 171, 172; 536/22.1, 23.1, 24.3–33; 204/155

(56) References Cited

U.S. PATENT DOCUMENTS

| | | |
|---|---|---|
| 5,143,854 | 9/1992 | Pirrung et al. . |
| 5,587,285 | * 12/1996 | Cloyd et al. .............................. 435/5 |
| 5,646,001 | * 7/1997 | Terstappen et al. ................. 435/7.21 |
| 5,688,648 | 11/1997 | Mathies et al. . |
| 5,707,804 | 1/1998 | Mathies et al. . |
| 5,728,528 | 3/1998 | Mathies et al. . |

(List continued on next page.)

FOREIGN PATENT DOCUMENTS

| | | |
|---|---|---|
| 0781853A2 | * 2/1997 | (EP) . |
| WO 98/00231 | 1/1998 | (WO) . |
| WO 98/00705 | 1/1998 | (WO) . |
| WO-98/18956-A1 | * 5/1998 | (WO) . |
| WO 98/45484 | 10/1998 | (WO) . |
| WO 99/16162 | 4/1999 | (WO) . |

OTHER PUBLICATIONS

Murakami et al NAR vol. 19, No. 15 pp. 4097–4102 1991.*
Egholm et al Nature vol. 365 pp. 566–568 1993.*
Stryer Biochemistry pp. 215–216 1990.*
Tyag, S. et al., "Molecular Beacons: Probes the Floresce upon Hybridization", *Nature Biotech,* (1996), 14:303–308.
Tyagi, S. et al., "Multicolor molecular beacons for allele discrimination", *Nature Biotech,* (1998), 16:49–53.
Walker, G.T. et al., "DNA detection be strand displacement amplification and fluorescence polarization with signal enhancement using a DNA binding protein," *Nucl. Acids Res.* (1996), 24(2):34–353.
PanVera Corporation "Fluorescence Polarization Applications Guide", Madison, WI.
U.S. application No. 09/321,309; Sundberg et al.

Primary Examiner—Kenneth R. Horlick
Assistant Examiner—Jeffrey Siew
(74) Attorney, Agent, or Firm—Matthew B. Murphy

(57) ABSTRACT

Methods, systems, kits for carrying out a wide variety of different assays that comprise providing a first reagent mixture which comprises a first reagent having a fluorescent label. A second reagent is introduced into the first reagent mixture to produce a second reagent mixture, where the second reagent reacts with the first reagent to produce a fluorescently labeled product having a substantially different charge than the first reagent. A polygon is introduced into at least one of the first and second reagent mixtures, and the fluorescent polarization in the second reagent mixture relative to the first reagent mixture is determined, this fluorescent polarization being indicative of the rate or extent of the reaction.

56 Claims, 15 Drawing Sheets

U.S. PATENT DOCUMENTS

| | | |
|---|---|---|
| 5,744,305 | 4/1998 | Fodor et al. . |
| 5,747,247 * | 5/1998 | Kowalcyzkowski et al. ............ 435/6 |
| 5,779,868 | 7/1998 | Parce et al. . |
| 5,783,687 * | 7/1998 | Glazer et al. ........................ 536/26.6 |
| 5,853,992 | 12/1998 | Glazer et al. . |
| 5,858,195 | 1/1999 | Ramsey . |
| 5,869,255 | 2/1999 | Mathies et al. . |
| 5,885,470 | 3/1999 | Parce et al. . |
| 5,925,558 * | 7/1999 | Tsien et al. ........................ 435/252.3 |
| 6,087,107 * | 7/2000 | Sheffield et al. .......................... 435/6 |
| 6,149,787 * | 11/2000 | Chow et al. .......................... 204/451 |
| 6,153,073 * | 11/2000 | Dubrow et al. ....................... 204/453 |

* cited by examiner

ASSAY METHODS AND SYSTEM

BACKGROUND OF THE INVENTION

Virtually all chemical, biological and biochemical research depends upon the ability of the investigator to determine the direction of her research by assaying reaction mixtures for the presence or absence of a particular chemical species within the reaction mixture. In a simple case, the rate or efficiency of a reaction is assayed by measuring the rate of production of the reaction product, or the depletion of a reaction substrate. Similarly, interactive reactions, e.g., binding or dissociation reactions are generally assayed by measuring the amount of bound or free material in the resultant reaction mixture.

For certain reactions, the species of interest, or a suitable surrogate, is readily detectable and distinguishable from the remainder of the reagents. Thus, in order to detect such species, one merely needs to look for it. Often, this is accomplished by rendering a reaction product optically detectable and distinguishable from the reagents by virtue of an optical signaling element or moiety that is only present or active on the product or the substrate. By measuring the level of optical signal, one can directly ascertain the amount of product or remaining substrate.

Unfortunately, many reactions of particular interest do not have the benefit of having a readily available surrogate reagent that produces signal only when subjected to the reaction of interest. For example, many reactions that are of great interest to the biological research field do not subject their reagents to the types of modifications that can give rise to substantial optical property changes. Researchers have attempted to engineer substrates, which give rise to optical property changes. For example, typical binding reactions between two molecules result in a bound complex of those molecules. However, even when one member of the binding pair is labeled, the formation of the complex does not generally give rise to an optically detectable difference between the complex and the labeled molecule. As a result, most binding assays rely upon the immobilization of one member or molecule of the binding pair. The labeled molecule is then contacted with the immobilized molecule, and the immobilizing support is washed. Following washing, the support is then examined for the presence of the labeled molecule, indicating binding of the labeled component to the unlabeled, immobilized component. Vast arrays of different binding member pairs are often prepared in order to enhance the throughput of the assay format. See, e.g., U.S. Pat. No. 5,143,854 to Pirrung et al.

Alternatively, in the case of nucleic acid hybridization assays, researchers have developed complementary labeling systems that take advantage of the proximity of bound elements to produce fluorescent signals, either in the bound or unbound state. See, e.g., U.S. Pat. Nos. 5,668,648, 5,707,804, 5,728,528, 5,853,992, and 5,869,255 to Mathies et al. for a description of FRET dyes, and Tyagi et al. Nature Biotech. 14:303–8 (1996), and Tyagi et al., Nature Biotech. 16:49–53 (1998) for a description of molecular beacons.

As noted above, binding reactions are but one category of assays that generally do not produce optically detectable signals. Similarly, there are a number of other assays whose reagents and/or products cannot be readily distinguished from each other, even despite the incorporation of optically detectable elements. For example, kinase assays that incorporate phosphate groups onto phosphorylatable substrates do not generally have surrogate substrates that produce a detectable signal upon completion of the phosphorylation reaction. Instead, such reactions typically rely upon a change in the structure of the product, which structural change is used to separate the reactants from the product. The separated product is then detected. As should be apparent, assays requiring additional separation steps can be extremely time consuming and less efficient, as a result of losses during the various assay steps.

It would generally be desirable to be able to perform the above-described assay types without the need for solid supports, additional separation steps, or the like. The present invention meets these and a variety of other important needs.

SUMMARY OF THE INVENTION

The present invention provides methods, systems, kits and the like for carrying out a wide variety of different assays. These assays typically comprise providing a first reagent mixture which comprises a first reagent having a fluorescent label. A second reagent is introduced into the first reagent mixture to produce a second reagent mixture, where the second reagent reacts with the first reagent to produce a fluorescently labeled product having a substantially different charge than the first reagent. A polyion is introduced into at least one of the first and second reagent mixtures, and the fluorescent polarization in the second reagent mixture relative to the first reagent mixture is determined, this fluorescent polarization being indicative of the rate or extent of the reaction.

Another aspect of the present invention is a method of detecting a reaction. The method comprises providing a first reagent mixture which contains a first reagent having a fluorescent label. A second reagent is introduced into the first reagent mixture to produce a second reagent mixture. The second reagent reacts with the first reagent to produce a fluorescently labeled product having a substantially different charge than the first reagent. A polyion is introduced into at least one of the first and second reagent mixtures and fluorescent polarization is compared in the second reagent mixture relative to the first reagent mixture.

A further aspect of the present invention is a method of identifying the presence of a subsequence of nucleotides in a target nucleic acid. The method comprises contacting the target nucleic acid sequence with an uncharged, fluorescently labeled nucleic acid analog in a first reaction mixture. The nucleic acid analog is complementary to the subsequence whereby the nucleic acid analog is capable of specifically hybridizing to the subsequence to form a first hybrid. The first reaction mixture is contacted with a polyion and the level of fluorescence polarization of the first reaction mixture in the presence of the polyion is compared to the level of fluorescence polarization of the uncharged nucleic acid analog in the absence of the target nucleic acid sequence. An increase in the level of fluorescence polarization indicates the presence of the first hybrid.

Another aspect of the present invention is a method of detecting the phosphorylation of a phosphorylatable compound. The method comprises providing the phosphorylatable compound with a fluorescent label. The phosphorylatable compound is contacted with a kinase enzyme in the presence of a phosphate group in a first mixture and then contacting the first mixture with a polyion. The level of fluorescence polarization from the first mixture in the presence of the polyion is compared to the level of fluorescence polarization from the phosphorylatable compound with the fluorescent label in the absence of the kinase enzyme.

A further aspect of the present invention is a method of detecting the phosphorylation of a phosphorylatable compound. The method comprises providing the phosphorylatable compound with a fluorescent label. The phosphorylatable compound is contacted with a kinase enzyme in the presence of a phosphate group in a first mixture. The first mixture is contacted with a second reagent mixture comprising a protein having a chelating group associated therewith, and a metal ion selected from $Fe^{3+}$, $Ca^{2+}$, $Ni^{2+}$ and $Zn^{2+}$. The level of fluorescence polarization from the first mixture in the presence of the second mixture is compared to the level of fluorescence polarization from the phosphorylatable compound with the fluorescent label in the absence of the kinase enzyme.

A further aspect of the present invention is an assay system comprising a fluid receptacle. The system contains a first reaction zone containing a first reagent mixture which comprises a first reagent having a fluorescent label, a second reagent that reacts with the first reagent to produce a fluorescently labeled product having a substantially different charge than the first reagent, and a polyion. The system also includes a detection zone and a detector disposed in sensory communication with the detection zone. The detector is configured to detect the level of fluorescence polarization of reagents in the detection zone.

Another aspect of the present invention is an assay system comprising a first channel disposed in a body structure. The first channel is fluidly connected to a source of a first reagent mixture which comprises a first reagent having a fluorescent label, a source of a second reagent that reacts with the first reagent to produce a fluorescently labeled product having a substantially different charge than the first reagent; and a source of a polyion. The system also includes a material transport system for introducing the first reagent, the second reagent and the polyion into the first channel and a detector disposed in sensory communication with the first channel. The detector is configured to detect the level of fluorescence polarization of reagents in the detection zone.

Another aspect of the present invention is a kit. The kit includes a volume of a first reagent which comprises a fluorescent label; a volume of a second reagent which reacts with the first reagent to produce a fluorescent product having a substantially different charge from the first reagent; and a volume of a polyion. The kit also includes instructions for determining the level of fluorescence polarization of the first reagent, mixing the first reagent, the second reagent and the polyion in a first mixture, determining the level of fluorescence polarization of the first mixture, and comparing the level fluorescence polarization of the first reagent to the level of fluorescence polarization of the first mixture.

Another aspect of the present invention is an assay system for quantifying a reaction parameter which comprises providing a first reagent mixture. The first reagent mixture includes a first reagent having a fluorescent label. A second reagent is introduced into the first reagent mixture to produce a second reagent mixture. The second reagent reacts with the first reagent to produce a fluorescently labeled product having a substantially different charge than the first reagent. A polyion is introduced into at least one of the first and second reagent mixtures. The system also includes a computer implemented process, comprising the steps of determining a first level of fluorescence polarization of the first reagent mixture; determining a second level of fluorescence polarization of the second reagent mixture; comparing the first and second levels of fluorescent polarization; and calculating the reaction parameter.

DETAILED DESCRIPTION OF THE INVENTION

I. Introduction

Figure 1:
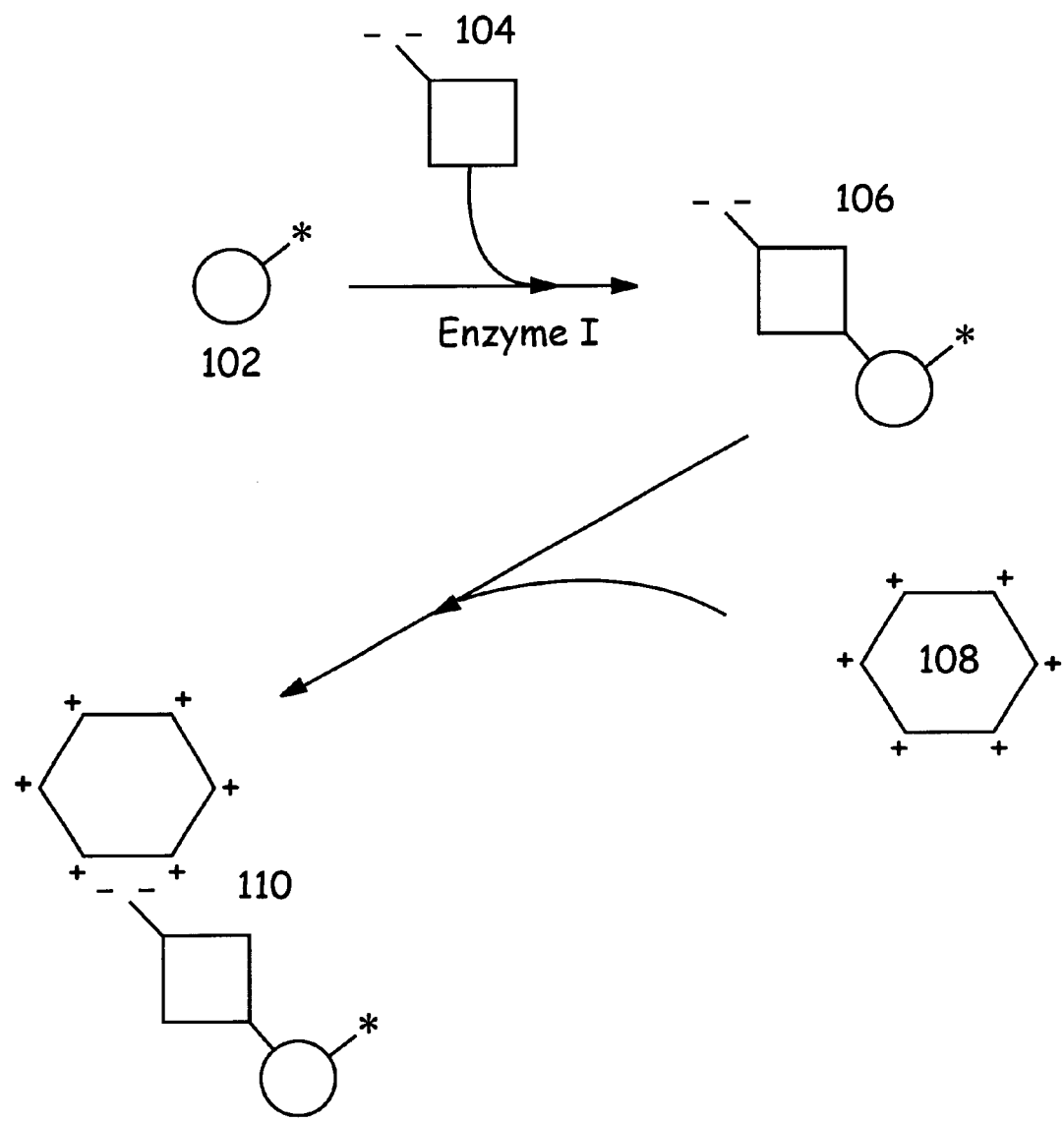
FIG. 1 is a schematic illustration of one embodiment of a general assay process performed in accordance with the present invention.

The present invention generally provides assay methods and systems which are broadly useful in a variety of different contexts where other typical assay formats cannot be used. The present methods and systems are capable of detecting a reaction product in the presence of the reaction substrate, despite the fact that the product is detected by virtue of a property that it shares with the reaction substrate, e.g., a fluorescent labeling group.

In general, the methods and systems of the present invention distinguish reaction product from a reaction substrate by virtue of a change in the level of charge between the two as a result of the reaction. The charge on one of these reaction components, whether it is located on the substrate or the product, is used to associate that component with a relatively large polyionic compound. The preferential association of the large polyionic compound with either the substrate or the product results in a substantial difference in the level of polarization of fluorescent emissions from that component when it is excited using polarized light. Because the large compound associates preferentially with only one of the substrate or product, as a result of the availability or elimination of charge due to the reaction of interest, that association and its consequent change in fluorescence polarization becomes an indicator of the progress of the reaction of interest.

II. Assay Methods

In at least one aspect, the present invention provides a method of detecting a chemical, biochemical or biological reaction. The method comprises providing a first reagent mixture, which comprises a first reagent having a fluorescent label. A second reagent is introduced into the first reagent mixture to produce a second reagent mixture. The second reagent is generally capable of reacting or otherwise interacting with the first reagent to produce a fluorescently labeled product having a substantially different charge than the first reagent. As used herein, the phrase "substantially different charge" means that the net charge on the product differs from that of the first reagent by an amount sufficient to permit the differential association of the substrate and product with a polyionic compound as described herein. This differential charge may be a fraction of a charge, on average over the entire reagent molecule. However, in preferred aspects, the substrate and product typically differ by at least one charge unit at the pH at which the assay is being performed. For example, a product that bears a net single positive or negative charge has a substantially different charge from a first reagent that has a net neutral charge, as the phrase is used herein. Similarly, a product that bears two positive charges has a substantially different charge from a first reagent that has a single positive charge. Preferably, a product having a substantially different charge than the first reagent will differ in net charge by at least two charge units, and in certain aspects, many more than two charge units difference, e.g., in the nucleic acid applications described in greater detail below.

A polyion is contacted with either or both of the first and second reagent mixtures, depending upon the assay type that is being performed, and the nature of the product produced by the reaction of interest. Because the reaction of interest produces a product with a substantially different charge than the substrate, that product will interact quite differently with the polyion than will the substrate, e.g., increased or decreased interaction/association. The association or lack of association has a profound effect on the ability of the product to depolarize emitted fluorescence. Specifically, and as described in greater detail below, the relatively small first reagent has a relatively fast rotational diffusion rate. This rotational diffusion rate is responsible for a fluorescent compound's ability to emit depolarized fluorescence when excited with polarized light. However, association of a large polyionic compound with a small fluorescent molecule will significantly slow the rate of rotational diffusion of that molecule, and reduce its ability to emit depolarized fluorescence.

The level of fluorescent polarization in the second reagent mixture is then compared to the level of fluorescent polarization from the first reagent mixture. By comparing these values, one can quantify the amount of fluorescence that is emitted from material bound to the polyion. As described in greater detail below, the assay is adjusted, e.g., by adjusting pH, ionic strength or the like, so that only one of the first reagent or product is capable of associating with the polyion. Thus, the change in fluorescence polarization is used to calculate a quantitative measure of the amount of product produced or first reagent consumed, and therefore becomes a measure of the reaction.

The principles behind the use of fluorescence polarization measurements as a method of measuring binding among different molecules are relatively straight-forward. Briefly, when a fluorescent molecule is excited with a polarized light source, the molecule will emit fluorescent light in a fixed plane, e.g., the emitted light is also polarized, provided that the molecule is fixed in space. However, because the molecule is typically rotating and tumbling in space, the plane in which the fluoresced light is emitted varies with the rotation of the molecule (also termed the rotational diffusion of the molecule). Restated, the emitted fluorescence is generally depolarized. The faster the molecule rotates in solution, the more depolarized it is. Conversely, the slower the molecule rotates in solution, the less depolarized, or the more polarized it is. The polarization value (P) for a given molecule is proportional to the molecule's "rotational correlation time," or the amount of time it takes the molecule to rotate through an angle of 57.3° (1 radian). The smaller the rotational correlation time, the faster the molecule rotates, and the less polarization will be observed. The larger the rotational correlation time, the slower the molecule rotates, and the more polarization will be observed. Rotational relaxation time is related to viscosity ($\eta$), absolute temperature (T), molar volume (V), and the gas constant (R). The rotational correlation time is generally calculated according to the following formula:

$$\text{Rotational Correlation Time} = 3\, \eta V/RT \qquad (1)$$

As can be seen from the above equation, if temperature and viscosity are maintained constant, then the rotational relaxation time, and therefore, the polarization value, is directly related to the molecular volume. Accordingly, the larger the molecule, the higher its fluorescent polarization value, and conversely, the smaller the molecule, the smaller its fluorescent polarization value.

In the performance of fluorescent binding assays, a typically small, fluorescently labeled molecule, e.g., a ligand, antigen, etc., having a relatively fast rotational correlation time, is used to bind to a much larger molecule, e.g., a receptor protein, antibody etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

Generally, the fluorescence polarization level is calculated using the following formula:

$$P = [I(\|) - I(\perp)] / [I(\|) + I(\perp)] \qquad (2)$$

Where $I(\|)$ is the fluorescence detected in the plane parallel to the excitation light, and $I(\perp)$ is the fluorescence detected in the plane perpendicular to the excitation light.

In performing screening assays, e.g., for potential inhibitors, enhancers, agonists or antagonists of the binding function in question, the fluorescence polarization of the reaction mixture is compared in the presence and absence of different compounds, to determine whether these different compounds have any effect on the binding function of interest. In particular, in the presence of inhibitors of the binding function, the fluorescence polarization will decrease, as more free, labeled ligand is present in the assay. Conversely, enhancers of the binding function will result in an increase in the fluorescent polarization, as more complex and less free-labeled-ligand are present in the assay.

As noted above, the assay methods of the present invention typically utilize a first reagent that includes a fluorescent labeling group. The nature of the first reagent generally depends upon the type of assay that is being performed. Typically, the assays that may be performed utilizing the present invention are myriad, including a wide range of binding or other associative assays, as well as assays of enzymatic activity. Accordingly, the first reagents, as described herein, generally include, e.g., one member of a specific binding pair, i.e., antibody/antigen pairs, receptor/ligand pairs, complementary nucleic acids or analogs thereof, binding proteins and their binding sites. Alternatively, or additionally, the first reagent may comprise a substrate which is modified by the reaction of interest, e.g., by addition to, subtraction from or alteration of the chemical structure of the first reagent. Some specific examples of such substrates include, e.g., kinase substrates which include phosphorylatable moieties, e.g., serine, threonine and tyrosine phosphorylation sites, and the like, phosphorylated substrates for phosphatase enzymes, amino or keto containing substrates subject to amino transferases, alcohols converted to carboxyls (e.g., via glucose-6-phosphate dehydrogenase), as well as substrates for: sulfatases; phosphorylases; esterases; hydrolases (e.g., proteases); oxidases, and the like.

The first reagent may be charged, either positively or negatively, or it may be neutral, depending upon the nature of the assay that is to be performed. The fluorescent label on the first reagent may be selected from any of a variety of different fluorescent labeling compounds. Generally, such fluorescent labeling materials are commercially available from, e.g., Molecular Probes (Eugene, Oreg.). Typically, fluorescein or rhodamine derivatives are particularly well suited to the assay methods described herein. These fluorescent labels are coupled to the first reagent, e.g., covalently through well known coupling chemistries. For a discussion of labeling groups and chemistries, see, e.g., Published International Patent Application No. WO 98/00231, which is incorporated herein by reference.

Also as noted above, the second reagent generally reacts, interacts or otherwise associates or binds with the first reagent to produce a fluorescent product that includes a substantially different charge than the first reagent. As with the first reagent, this second reagent optionally comprises one member of a specific binding pair, e.g., the member that is complementary to the first reagent, provided that the hybrid of the two members of the binding pair, or first and second reagents, bears a charge that is substantially different from the charge of the first reagent member of the binding pair. In many cases, this involves a second reagent that is charged while the first reagent is neutral, or a second reagent that is highly charged as compared to a first reagent that is only moderately charged. Alternatively, the association of the first and second reagents confers a conformational change that yields a charged product, or binds to and masks charged residues on the first reagent.

Because the product produced by the interaction of the first and second reagents has a different charge than the first reagent alone, it will interact differently with other charged molecules. In particular, polyionic compounds that bear a substantial number of charges will generally interact with charged materials in a charge dependent manner. In the case of the present invention, large polyionic compounds are used in order to "tag" the product (or in some cases, the first reagent) with a relatively large compound that will affect the product's ability to emit depolarized fluorescence.

Preferred polyions for use in the present invention include polyamino acids, e.g., proteins, polypeptides, i.e., polylysine, polyhistidine, and polyarginine. Other polyions that are useful in accordance with the invention include organic polyions, i.e., polyacrylic acid, polycarboxylic acids, polyamines (e.g., polyethylamine), polysulfonic acids (e.g., polystyrene sulfonic acid) polyphosphoric acid (e.g., polyvinylphosphoric acid), or copolymers of any or all of these, e.g., mixed polymers of these polyamino acids, and the like. These polyions are typically relatively large in comparison to the first and/or second reagents, and/or the product that is being used in the assay of interest. As such, the size of the polyion may vary depending upon the size of the first and/or second reagents and/or the product. Typically, the polyion will range in size from about 5 kD to about 1000 kD, and preferably, from about 10 kD to about 100 kD. In the case of polyamino acids, this typically constitutes a polymer of from about 50 to about 10,000 amino acid monomers in length, and preferably from about 100 to about 1000 monomers in length.

The polyions used in accordance with the present invention are generally capable of interacting with the other components of the reaction mixture in a non-specific charge dependent manner. As a non-specific interaction, it will be appreciated that the polyions used in accordance with the present invention do not require the presence of a specific recognition site in the product (or substrate). This non-specific interaction thus provides for a broader applicability for the assays of the present invention. Also as noted, the polyion interacts with the product (or substrate) is a charge dependent fashion. As a result, in the case of titratable polyions, this can require buffer conditions that permit the presence of the charges used in that interaction. Typically, polyionic materials preferably will have an isoelectric point (pI) that provides a significant level of charge at the relevant pH level for the assay conditions. Typically, buffers in which the assays of the present invention are carried out will typically be in the physiologically relevant range, e.g., from about pH 6 to about pH 8, at which, the polyionic compounds will have a sufficient charge level to interact with charged reagents. However, as will be appreciated, one can generally adjust the level of charge, and thus the level of interaction between a polyion and a product (or substrate) by adjusting the buffer in which these elements are disposed, thereby effecting the charge level of one or both of the polyion or the product. Routine reaction tuning can also be used to optimize any given assay to yield optimal reaction rates as well as interaction between the polyionic component and the product (or substrate).

The differential interaction between the polyion and the fluorescent product, as compared to its interaction with the fluorescent first reagent is then used as a means for comparing the amount of product produced. Specifically, a relatively small fluorescent compound, e.g., the first reagent, generally emits relatively depolarized fluorescence when it is excited by polarized excitation light. This is generally due to the faster rotational diffusion or "spin" of these smaller compounds. Larger compounds, on the other hand have slower spin and thus are more likely to emit relatively polarized fluorescence when excited by a polarized excitation light source. By tagging the product with a large "label" in the form of a polyion, one substantially alters the product's ability to emit depolarized fluorescence. This property is then detected and quantified as a measure of the reaction of the first and second reagents. Typically, the detected fluorescence polarization, or P value, provides a measure of the ratio of bound label to free label, although assay results may also be determined as a difference between pre-reaction fluorescence polarization and post-reaction fluorescence polarization, with the difference being an indication of the reaction's rate and/or completeness.

FIG. 1 schematically and generally illustrates the assay methods of the present invention. These illustrations are for example purposes only and are not intended to imply limits to the present invention. Briefly, as shown in FIG. 1, a fluorescently labeled first reagent 102 is provided. The first reagent has a relatively fast rotational diffusion rate. The first reagent 102 is contacted with a second reagent, e.g., Enzyme I, which either mediates addition of or itself constitutes a charged group 104 that associates with the first reagent 102 to create a charged product 106. The resulting charged product typically has a rotational diffusion rate that is not substantially different from that of the first reagent.

The product is then contacted with a relatively large polyion 108, which associates with the charged fluorescent product 106. The resulting polyion/charged fluorescent product 110 has a substantially reduced rotational diffusion rate as compared to the original first reagent. As described above, this difference in rotational diffusion rate is quantitatively measurable using, e.g., fluorescent polarization detection methods.

Although generally described in terms of the polyion associating with the product of the reaction of interest, the methods described herein also operate in the reverse direction. Specifically, the first reagent optionally is associated with the polyion, with all of the characteristics that entails. The reaction of interest then alters the charge of the first reagent in producing a product. The product then has a reduced or eliminated interaction with the polyion as compared to the first reagent. This reduced interaction then gives rise to a change in the product's ability to emit polarized fluorescence relative to the first reagent. In some cases, this may require that the assay utilize a heterogeneous format, e.g., introducing the polyion after the reaction of interest is carried out, as a result of potential interfering effects of the polyion on the reaction of interest. Methods of performing the assay methods of the invention in both homogeneous and heterogeneous formats are described in greater detail below.

The level of fluorescence polarization of the product then provides an indication of the amount of the fluorescent label that is bound to the polyion, e.g., as the ratio of bound to free label. Typically, fluorescence polarization data are generally reported as the ratio of the difference of parallel and perpendicular fluorescence emissions to the sum of these fluorescent emissions. Thus, the smaller the difference between these fluorescence emissions, e.g., the more depolarized the emissions, the smaller the polarization value. Conversely, more polarized emissions yield larger numbers. As alluded to above, in comparing assay results, the polarization value (P) for the reaction mix is determined. The fraction of bound fluorescence, e.g., associated with the polyion, is determined as:

$$F_b = (P - P_f)/(P_b - P_f) \quad (3)$$

where $P_b$ is the P value of the bound species, and $P_f$ is the P value of the free species. Thus, the polarization value can be used as an absolute quantitative measurement of the ratio of product to substrate, where one has determined or is already aware of the P value for completely bound label and completely free label. Alternatively, as noted above, one can measure the pre-reaction and post reaction fluorescence polarization, using the difference between the two as an indication of the amount of product produced. As noted above, the assay methods also works for the inverted assay format, e.g., where the polyion is associated with the first reagent, but not the fluorescent product. In this case, the difference between the fluorescent polarization of the first reagent and the product is determined.

The P value serves as an indicator of the reaction of interest, e.g., by indicating the amount of product produced. As will be discussed in greater detail below, once an assay reaction is quantifiable, one can use that assay in a number of different applications, including for example diagnostics, but particularly for screening of potential inhibitors or enhancers of the reaction of interest. This is typically useful in screening compound libraries against pharmacologically relevant targets that utilize one or more of the reactions described herein, e.g., binding, enzymatic modification and the like.

Although generally described in terms of detection of fluorescent polarization, it will be readily appreciated that a variety of detection schemes may be employed which detect the rate of rotation of a molecule or the translation or lateral diffusion of a molecule that relates to the size of the molecule. Examples of methods of detecting a molecule's rotation include, e.g., nuclear magnetic resonance spectroscopy, electron spin resonance spectroscopy, and triplet state absorbance anisotropy. Examples of methods of detecting the translation rate of molecules include, e.g., fluorescent correlation spectroscopy, fluorescence recovery after photo bleaching, and magnetic resonance spin exchange spectroscopies.

As noted repeatedly above, the general methods and systems of the present invention can be used in assaying a variety of different types of biologically or biochemically relevant reactions, including enzyme mediated reactions, binding reactions and hybridization reactions. In the case of binding reactions, the first reagent that bears a fluorescent label is contacted with a second reagent that binds to the first reagent to yield a fluorescently labeled product. The second reagent typically includes a level of charge such that the product resulting from the binding of the second reagent to the first reagent has a charge that is substantially different than the first reagent alone.

A simple example of such a binding assay is a nucleic acid hybridization assay. Specifically, in determining the presence of a particular nucleic acid sequence or subsequence in a sample or target nucleic acid, one often interrogates the target nucleic acid with shorter nucleic acid probes that have a nucleotide sequence that is complementary to, and thus is capable of hybridizing to the sequence or subsequence of interest in the target. If the probe hybridizes to the target sequence, the presence of the subsequence of interest is indicated. Previously described high throughput methods have generally required that at least one of the probe or the target sequence is immobilized, e.g., on a solid support or in a particular position in an oligonucleotide array (See, e.g., U.S. Pat. Nos. 5,143,854 and 5,744,305). While some solution based hybridization detection methods have been described, these typically require specially synthesized reagents for the sequence that is to be interrogated, e.g., including FRET dye pairs, molecular beacons, or the like.

In the case of the present invention, the first reagent is typically an uncharged or positively charged nucleic acid analog, which bears a fluorescent label. Suitable nucleic acid analogs are generally known and include, e.g., peptide nucleic acids (PNAs), methyl phosphonate polymers and cationic nucleic acid analogs. Because these nucleic acid analogs are neutral, or in some cases positively charged, they do not form a charge based association with the polycation component of the assay.

Figure 2:
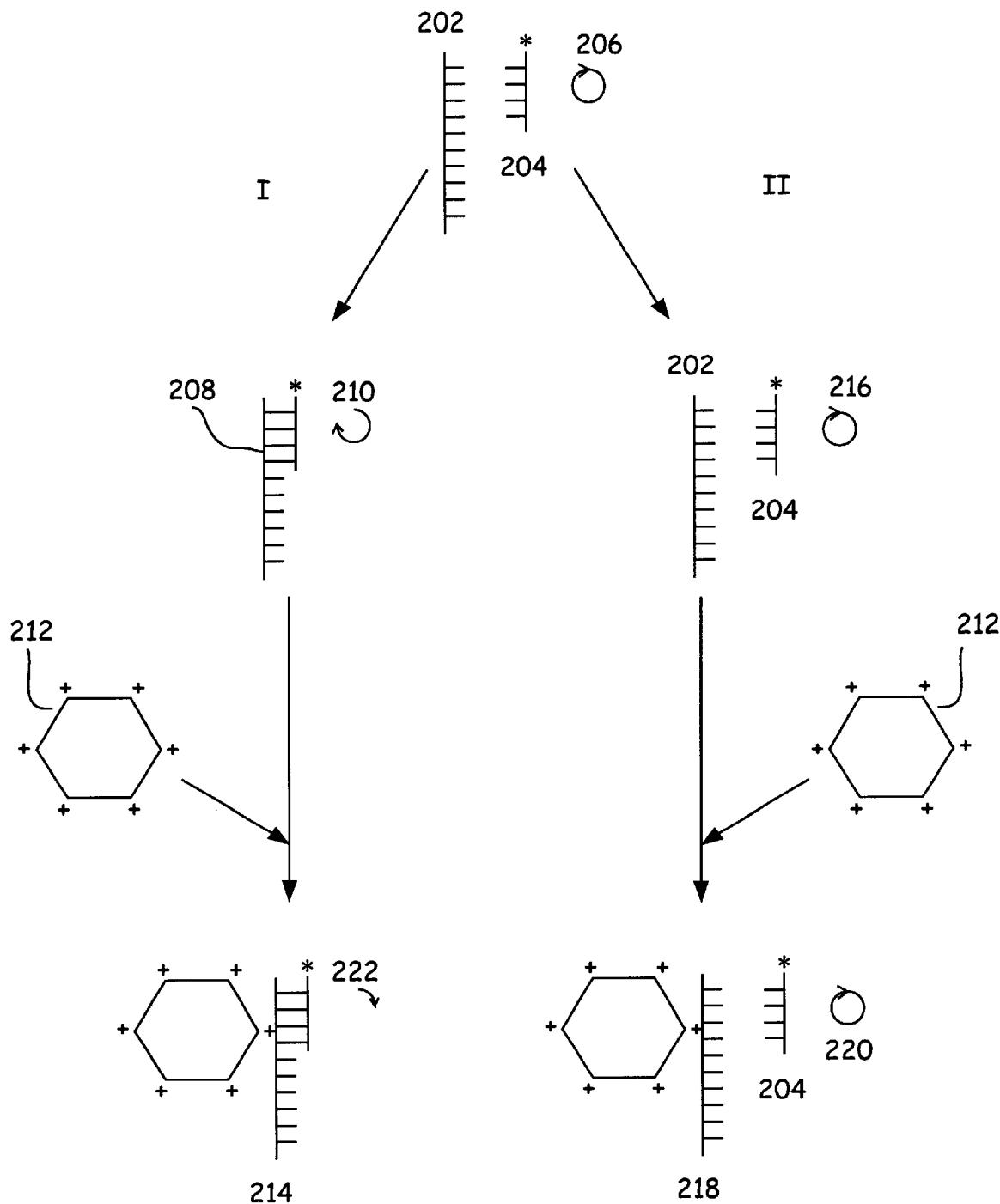
FIG. 2 is a schematic illustration of a binding assay, e.g., a nucleic acid hybridization assay, performed in accordance with the present invention.

Because nucleic acids are highly charged species, an uncharged or positively charged nucleic acid analog is used as the first reagent. This permits differentiation between the free probe and the probe that is hybridized to the target sequence by virtue of the charge on the hybrid from the presence of the target sequence. Although the polyion will associate with all of the target sequence, including that which does not hybridize to the probe, that interaction is invisible to the investigator, as the result of that interaction not bearing a fluorescent label. This nucleic acid hybridization assay is schematically illustrated in FIG. 2.

As shown, a target nucleic acid 202 (schematically illustrated) is interrogated with a fluorescent probe 204 (the fluorescent label is indicated as an *), which typically comprises an uncharged nucleic acid analog, e.g., a PNA probe. The probe is selected to be complementary to a particular nucleotide sequence, e.g., the sequence of interest, such that the probe will selectively hybridize to that sequence if it is present in the target nucleic acid 202. In its individual form, the probe will have a relatively high rate of rotational diffusion due to its small size, as schematically illustrated by arrow 206, thereby emitting more highly depolarized fluorescence.

The reaction illustrated in panel I illustrates the case where the target sequence 202 contains the sequence of interest, so that the probe 204 will hybridize to the target sequence 202 to form a first hybrid 208. Due to the larger size of the hybrid relative to that of the probe, this hybridization reaction will result in a reduction in the rotational rate of diffusion of the fluorescently labeled compound (in this case, the hybrid), as indicated by arrow 210. However, due to the flexible nature of nucleic acids, as well as the only incremental increase in size of the hybrid over that of the target, this reduction may not be substantial, and may not be easily detectable. In accordance with the methods of the present invention, however, this signal (P) is effectively amplified by adding a polyionic compound 212 to the hybrid. Specifically, nucleic acids, i.e., the target sequence, are highly charged species due to their negatively charged phosphate/sugar backbones. Thus, this charge exists even when the nucleic acid exists in double stranded form.

When a polyionic compound, e.g., polycation 212, i.e., polylysine, is added to the hybrid 208, it associates with the hybrid 208, in an associative complex 214, thereby substantially decreasing the rotational diffusion of the overall complex 214, as schematically illustrated by arrow 222. This difference is more readily detected.

In contrast, the reaction illustrated in panel II illustrates the instance where the target sequence 202 does not include the sequence of interest that is complementary to the sequence of the fluorescent probe 204. As such, the probe and target sequence are unable to hybridize, and the rotational diffusion of the fluorescent component (the unhybridized probe) remains unchanged as illustrated by arrow 216. Further, when the polycationic polyion is added to the reaction, it will again associate with the highly charged target sequence as an associative complex 218. However, the polycation will not associate with the fluorescent probe 204 due to the probe's uncharged character. As such, the rotational diffusion of the fluorescent compound (again the unhybridized probe 204) will remain unchanged, as illustrated by arrow 220. As a result, in the case where hybridization occurs, i.e., the sequence of interest is present in the target, the fluorescence emissions from the reaction, when excited by polarized excitation light, is substantially polarized as compared to that of the unhybridized probe. Conversely, where no hybridization occurs, i.e., the sequence of interest is not present, there is no change in the level of fluorescence polarization. Accordingly, a change in fluorescence polarization becomes an indicator of the presence of the sequence of interest.

The methods and systems of the present invention are also useful in carrying out a variety of other binding assays, where the resulting complex has a substantially different charge from the charge of a fluorescently labeled member of the binding pair. For example, in a receptor binding assay where a neutral, fluorescent ligand is bound to the charged, unlabeled receptor, the methods of the present invention serve to amplify a fluorescence polarization signal from the complex by associating a large polyionic compound with that complex. Specifically, while the complex will, by itself, give a fluorescence polarization response, as described herein, the complex with the associated polyionic compound will be substantially greater. As will be appreciated, a wide variety of binding assays may be carried out in accordance with the present invention. Even a greater number of assays may be readily configured to function in accordance with these methods, e.g., where the bound complex has a substantially different charge than a fluorescently labeled free member of the ultimate complex.

The methods and systems of the present invention also find particular usefulness in assaying for enzymatic activity where that activity produces a product that has a substantially different charge than the substrate upon which the enzyme acted. One example of a class of enzyme assays that is suited for the methods and systems of the present invention are those that add or remove phosphate groups to or from appropriate substrates, e.g. kinase and phosphatase assays. Interest in these activities is substantial due to their roles in mediating a wide variety of biologically relevant response reactions in vivo. In particular, kinase and phosphatase reactions are often precursor, or intermediate signaling events in complex cellular behaviors such as survival and proliferation. As such, their activities become of particular interest in addressing diseases where these behaviors are malfunctioning, e.g., cancer, and the like.

As noted above, the present invention is particularly useful in assaying for the activity of kinase enzymes. Kinase enzymes typically function by adding a phosphate group to a phosphorylatable substrate, e.g., protein, peptide, nucleoside, carbohydrate, etc. As phosphate groups are highly charged, their addition to a particular substrate typically imparts a substantial change in charge of the product over the substrate. As with the assays described above, this change in charge in the product over that of the substrate can be exploited by adding a polyionic compound that imparts a significant difference in the fluorescence polarization of the product over the substrate.

Briefly, a phosphorylatable substrate is provided with a fluorescent labeling group, as described above. The phosphorylatable substrate may be neutral or it may be charged. Preferred substrates are neutral under the relevant assay conditions. A variety of phosphorylatable substrates are commercially available. For example, rhodamine labeled substrate for protein kinase A (PKA) is generally commercially available from Promega Inc., while other fluorescent phosphorylatable substrates may be obtained from Research Genetics, Inc.

Because the fluorescent phosphorylatable substrate is typically relatively small, e.g., less than about 2 kD, it has a relatively high rate of rotational diffusion and thereby emits depolarized fluorescence when excited with polarized light. When contacted with a kinase enzyme in the presence of a phosphate donor group, e.g., ATP, the substrate is phosphorylated, imparting two additional negative charges for each phosphate incorporated. This net −2 charge, particularly in the case of the previously uncharged substrate, provides a basis for interaction of the product with a polyionic compound, e.g., a polycation such as polylysine or polyhistidine. Once the polyion associates with the phosphorylated substrate, it significantly slows the rate of rotational diffusion, and thereby reduces the rate of fluorescence depolarization, e.g., increases the fluorescence polarization value. This change in polarization is then detected and used to quantify the kinase reaction.

Figure 3:
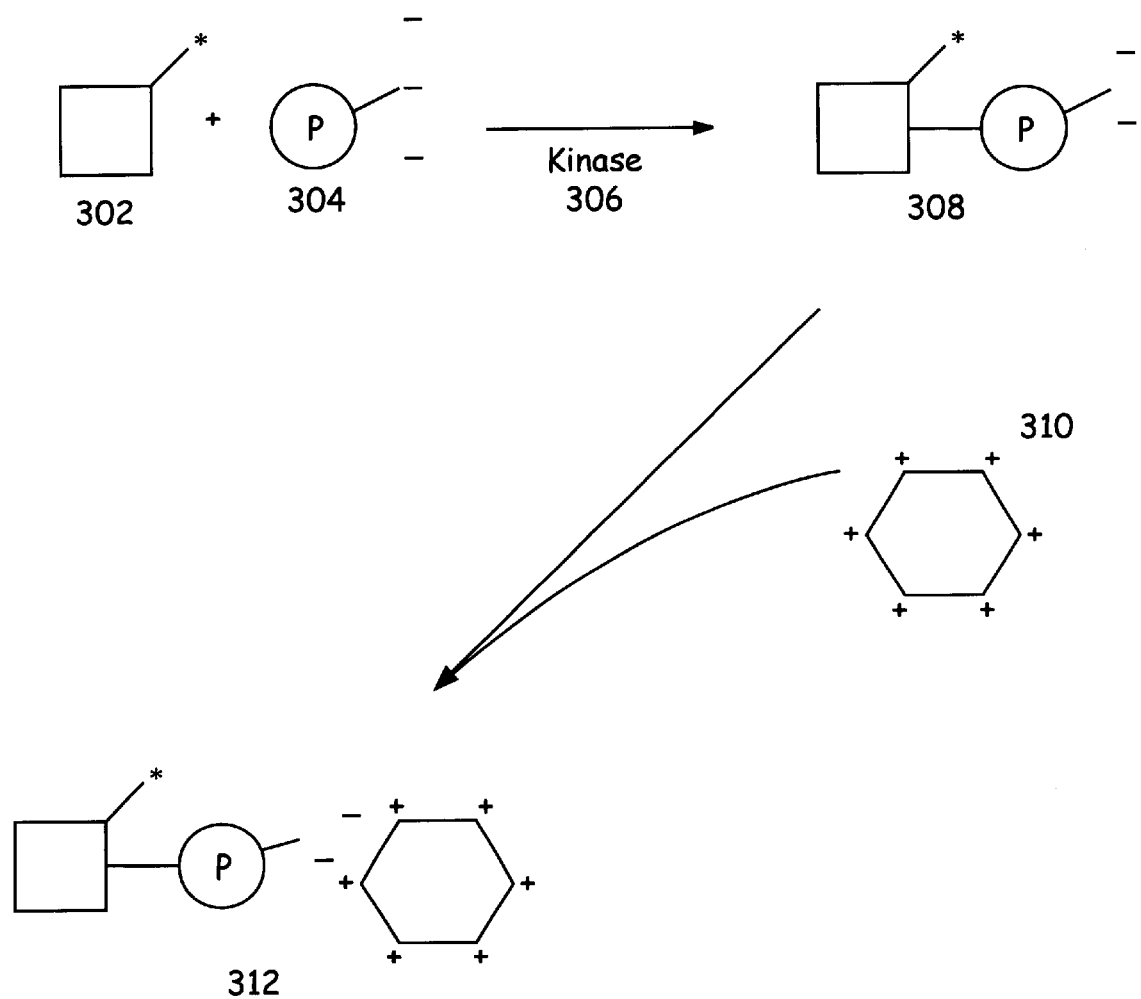
FIG. 3 is a schematic illustration of an enzyme assay, e.g., a kinase assay, performed in accordance with the present invention.

A schematic illustration of this reaction is shown in FIG. 3. As shown, the fluorescently labeled phosphorylatable substrate 302 is contacted with a kinase enzyme 306, in the presence of phosphate 304, e.g., in the form of ATP. The reaction yields the phosphorylated product 308. Both the fluorescent substrate 302 and the phosphorylated fluorescent product 308 have relatively high rates of rotational diffusion due to their small size. The fluorescent phosphorylated product is then contacted with a polycation. Preferred polycations include polyamino acids such as polylysine, polyhistidine or the like, with polyhistidine being most preferred. The polycation then associates with the negatively charged phosphorylated fluorescent product, thereby drastically affecting its size and rotational diffusion rate, which is then detected as described repeatedly herein. As will be appreciated, the polyionic component may alternatively comprise a large molecule, e.g., a protein or the like, that has associated therewith multivalent metal cations selected from, e g., $Fe^{3+}$, $Ca^{2+}$, $Ni^{2+}$ and $Zn^{2+}$. Examples of such molecules include metal chelating proteins that chelate these ions, or the like. Specifically, these metal ions have relatively high affinity for oxygen, nitrogen and sulfur groups. As a result, they can impart a significant binding affinity to a large molecule (as a polyion) towards, e.g., phosphate groups in nucleic acids or phosphorylated substrates and the like, as well as other groups bearing oxygen, nitrogen or sulfur groups, giving rise to the interaction that is used to significantly slow the rotational diffusion rate of a fluorescent species, as described herein.

Figure 4:
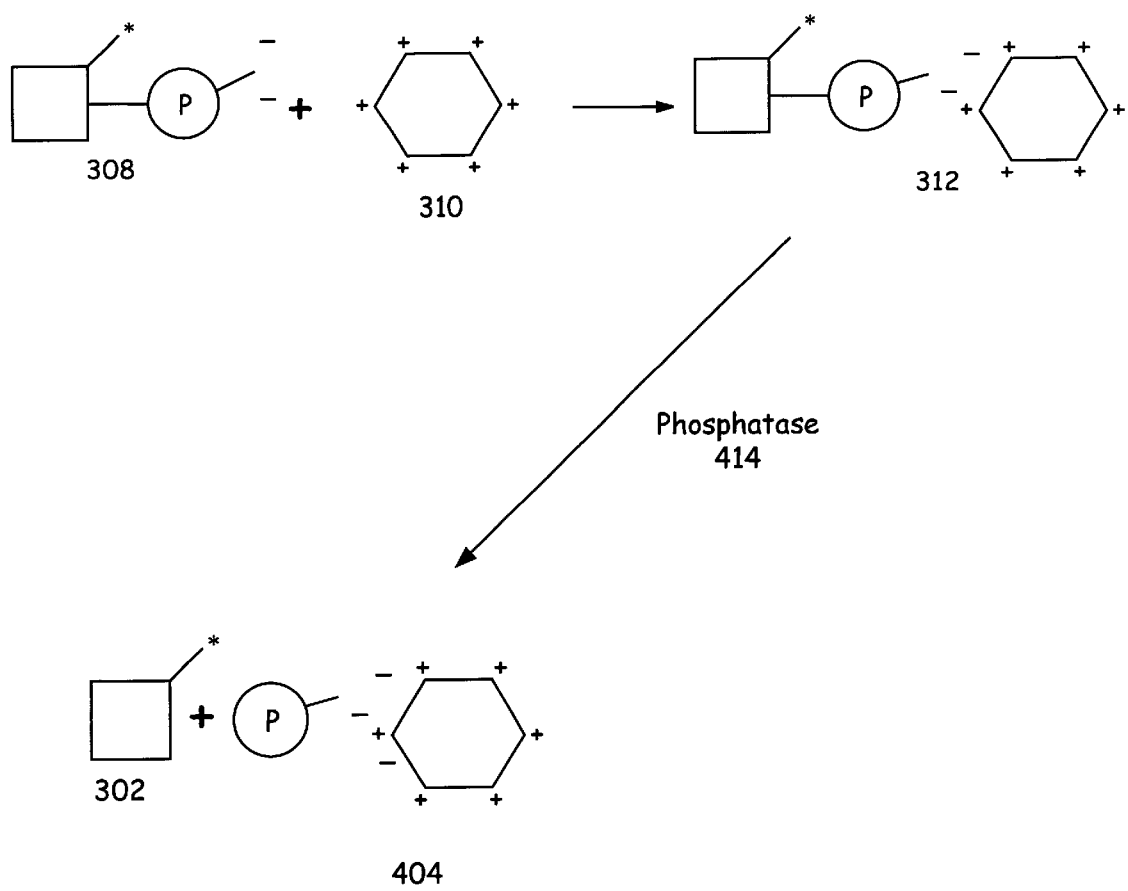
FIG. 4 is a schematic illustration of a phosphatase assay performed in accordance with the present invention.

The present invention is also well suited to assay the reverse reaction. Specifically, the phosphatase reaction, which removes a phosphate group from a phosphorylated substrate. This reaction follows substantially the reverse path of that shown in FIG. 3, and is schematically illustrated in FIG. 4. Briefly, the fluorescent phosphorylated compound 308, which in this instance is the substrate, is contacted with the polycationic compound 310 to yield the associative complex 312 where the polycation associates with the charges imparted by the phosphate group. As noted above with reference to FIG. 3, this complex has a slow rate of rotational diffusion. When this complex is acted on by a phosphatase enzyme 414 it results in cleavage of the charged phosphate group and its associated polycation 404 from the fluorescent component 302, which in this instance is the product. When free of the large polycationic compound, the fluorescent product has a greatly increased rate of rotational diffusion, e.g., emitting depolarized fluorescence. Again, this change in fluorescence polarization is detected as described herein. As noted above, in some cases, the assay may preferably be performed in a heterogeneous format, e.g., where the polyionic component is added after the reaction of interest, in order to avoid any adverse effects of the presence of the polyion on the reaction.

While the ability to perform a variety of assays is itself useful, the specific applications to which these assays are put typically provides the greatest value. Of particular interest is the ability to test the effects of potential pharmaceutical candidate compounds on the various activities described above. Specifically, in pharmaceutical discovery processes, large libraries of chemical compounds are generally screened against pharmacologically relevant targets. These targets may include receptors, enzymes, transporters, and the like. A variety of screening assays and systems have been described. See, e.g., Published International Patent Application No. WO 98/00231, which is incorporated herein by reference.

In brief, a particular reaction that is biologically or biochemically relevant is carried out in the presence and absence of a compound that is to be screened, and the effect of the compound is determined. Specifically, if the reaction is slowed or blocked by the presence of the test compound, then the compound is identified as an inhibitor of the reaction. Conversely where the reaction proceeds more rapidly or to a greater extent in the presence of the test compound, then the compound is identified as an enhancer of the reaction. These screening assays are then performed for a large number of different compounds, either serially or in parallel, in order to expedite the discovery of potential effectors of the reaction of interest.

III. Assay Systems

The present invention also provides assay systems that are used in carrying out the above-described methods. Typically, the assay systems described herein comprise a fluid receptacle into which the reagents are placed for performing the assay. The fluid receptacle typically comprises a first reaction zone having disposed therein a first reagent mixture which comprises a first reagent having a fluorescent label, a second reagent that reacts with the first reagent to produce a fluorescently labeled product having a substantially different charge than the first reagent and a polyionic compound.

Figure 5:
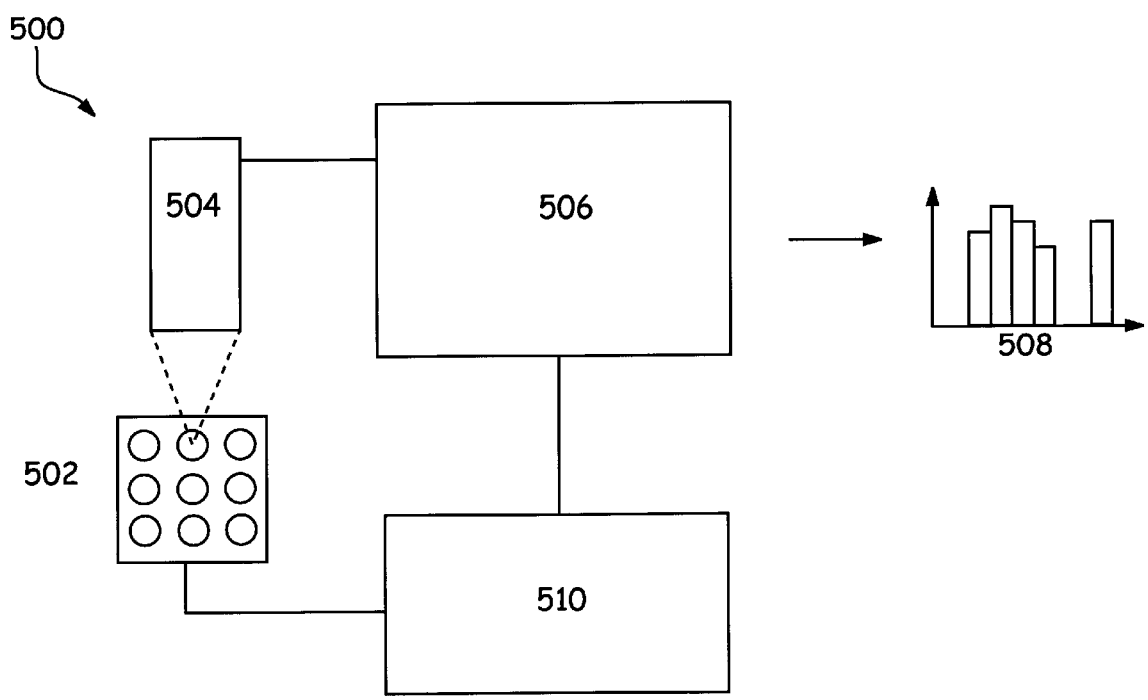
FIG. 5 is a general schematic illustration of an overall system used to carry out the assay methods of the present invention.

FIG. 5 schematically illustrates an overall assay system for use in practicing the present invention. Briefly, the overall system 500 includes a reaction receptacle 502, as described above. A detector or detection system 504 is disposed adjacent to the receptacle and within sensory communication of the receptacle. The phrase "within sensory communication" generally refers to the detector that is positioned relative to the receptacle so as to be able to receive a particular signal from that receptacle. In the case of optical detectors, e.g., fluorescence or fluorescence polarization detectors, sensory communication typically means that the detector is disposed sufficiently proximal to the receptacle that optical, e.g., fluorescent signals are transmitted to the detector for adequate detection of those signals. Typically this employs a lens, optical train or other detection element, e.g., a CCD, that is focused upon a relevant portion of the receptacle to efficiently gather and record these optical signals.

Detector 504 is typically connected to an appropriate data storage and/or analysis unit, e.g., a computer or other processor, which is generally capable of storing, analyzing and displaying the obtained data from the receptacle in a user comprehendible fashion, e.g., display 508. In certain embodiments, e.g., those employing microfluidic receptacles, the computer 506 is optionally connected to an appropriate controller unit 510, which controls the movement of fluid materials within the channels of the microfluidic device receptacle, and/or controls the relative position of the receptacle 502 and detector 504, e.g., via an x-y-z translation stage.

The receptacle also typically includes a detection zone as well as a detector disposed in sensory communication with the detection zone. The detector used in accordance with the present invention typically is configured to detect a level of fluorescence polarization of reagents in the detection zone.

As used herein, the receptacle may take on a variety of forms. For example, the receptacle may be a simple reaction vessel, well, tube, cuvette, or the like. Alternatively, the receptacle may comprise a capillary or channel either alone or in the context of an integrated fluidic system that includes one or more fluidic channels, chambers or the like.

In the case of a simple reaction vessel, well, tube, cuvette or the like, the reaction zone and the detection zone typically refer to the same fluid containing portion of the receptacle. For example, within the fluid containing portion of a cuvette, reagents are mixed, reacted and subsequently detected. Typically, in order to expedite the process of performing assays, e.g., screening assays, multiplexed receptacles may be used. Examples of such receptacles include, e.g., multiwell plates, i.e., 96-well, 384-well or 1536-well plates.

For capillary or channel based aspects, the reaction zone and the detection zone may comprise the same fluid-containing portion of the receptacle. However, in many aspects, the reaction zone and the detection zone are separate fluid containing portions of the receptacle. Specifically, reagents may be mixed and reacted in one portion of the receptacle, and subsequently moved to a separate detection zone whereupon the reaction products, etc. are detected.

In particularly preferred aspects, the receptacle comprises a microfluidic device. As used herein, the term "microfluidic device" refers to a device or body structure which includes and/or contains at least one fluidic component, e.g., a channel, chamber, well or the like, which has at least one cross sectional dimension that is between about 0.1 and about 500 $\mu$m, with these channels and/or chambers often having at least one cross-sectional dimension between about 0.1 $\mu$m and 200 $\mu$m, in some cases between about 0.1 $\mu$m and 100 $\mu$m, and often between about 0.1 $\mu$m and 20 $\mu$m. Such cross-sectional dimensions include, e.g., width, depth, height, diameter or the like. Typically, structures having these dimensions are also described as being "microscale." Microfluidic devices in accordance with the present invention, typically include at least one, and preferably more than one channel and/or chamber disposed within a single body structure. Such channels/chambers may be separate and discrete, or alternatively, they may be fluidly connected. Such fluid connections may be provided by channels, channel intersections, valves and the like. Channel intersections may exist in a number of formats, including cross intersections, "T" intersections, or any number of other structures whereby two channels are in fluid communication.

Because of their controllability, microfluidic device embodiments of the present invention are particularly useful in carrying out heterogeneous forms of the assays described herein. In particular, reactions are performed in a first region of the microscale channel network. The products of the reaction are then moved to a different portion of the channel network, or additional components are brought into the original portion of the channel network to mix with the products of the reaction. For example, the polyionic component of the assay methods described herein can be added after the reaction of interest to ensure that it does not interfere with the reaction. Microfluidic systems provide the ability to precisely move the various reagents through the various channels of the device, permitting their accurate measurement and timely addition. By way of a simple example, a phosphatase reaction may be carried out on a phosphorylated substrate in a first channel region of a microfluidic device, yielding a phosphate group, e.g., ATP, and the unphosphorylated product, as well as unreacted substrate. The mixture is then mixed with the polyionic component, e.g., polyhistidine, either by moving the reaction mixture to a separate channel containing the polyion or by introducing the polyion into the reaction mixture in the original channel segment. The resulting mixture is then moved past a detection point where the fluorescence polarization is measured.

The body structure of the microfluidic devices described herein typically comprises an aggregation of two or more separate components which when appropriately mated or joined together, form the microfluidic device of the invention, e.g., containing the channels and/or chambers described herein. Typically, the microfluidic devices described herein are fabricated as an aggregate of substrate layers. In particular, such preferred devices comprise a top portion, a bottom portion, and an interior portion, wherein the interior portion substantially defines the channels and chambers of the device.

Figure 6:
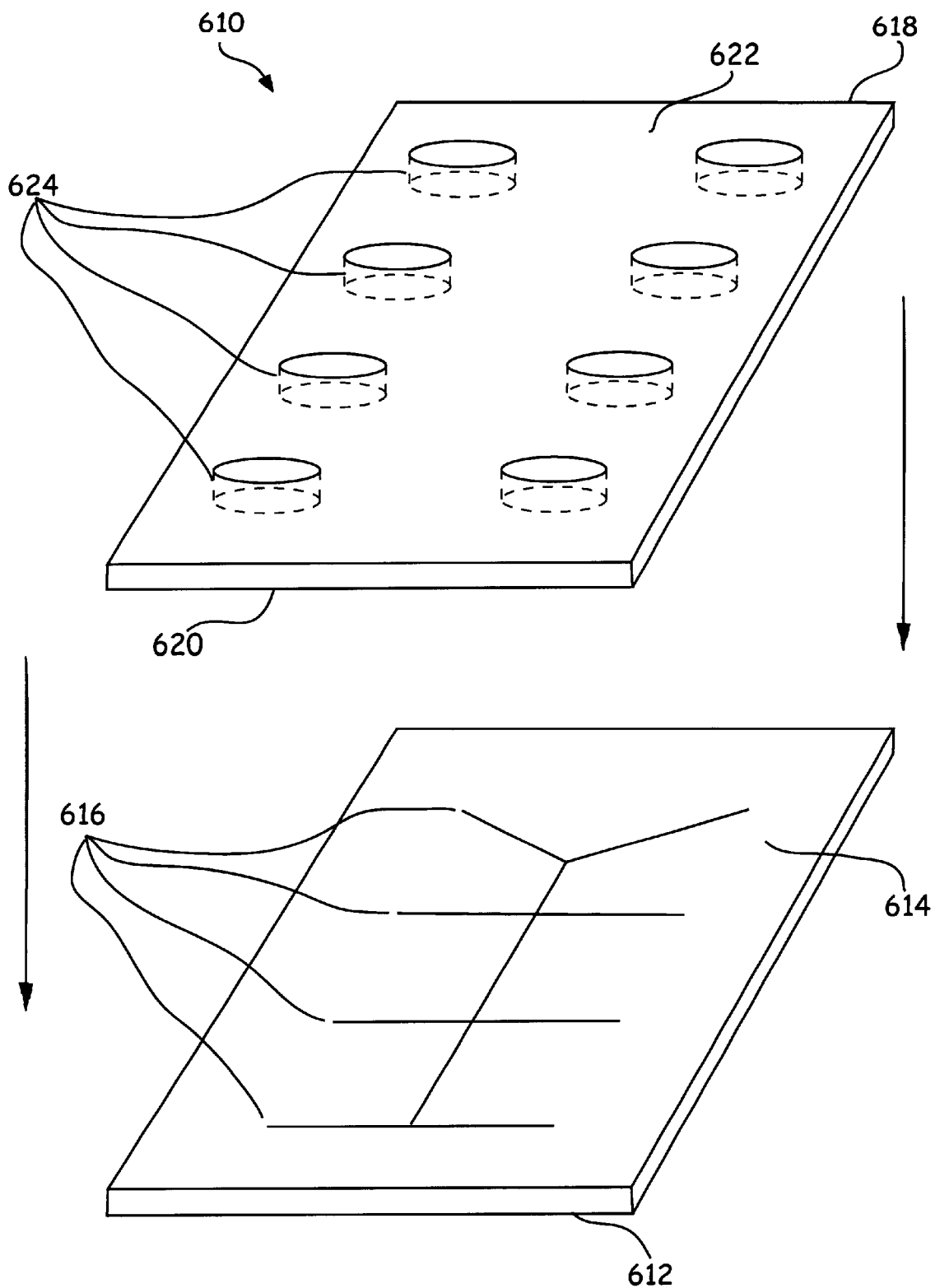
FIG. 6 is a schematic illustration of a multi-layered microfluidic device that is optionally employed as a reaction/assay receptacle in the present invention.

FIG. 6 illustrates a two-layer body structure 610, for a microfluidic device. In preferred aspects, the bottom portion of the device 612 comprises a solid substrate that is substantially planar in structure, and which has at least one substantially flat upper surface 614. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric 15-materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping or the like. Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, which is incorporated herein by reference in its entirety for all purposes.

The channels and/or chambers of the microfluidic devices are typically fabricated into the upper surface of the bottom substrate or portion 612, as microscale grooves or indentations 616, using the above described microfabrication techniques. The top portion or substrate 618 also comprises a first planar surface 620, and a second surface 622 opposite the first planar surface 620. In the microfluidic devices prepared in accordance with the methods described herein, the top portion also includes a plurality of apertures, holes or ports 624 disposed therethrough, e.g., from the first planar surface 620 to the second surface 622 opposite the first planar surface.

The first planar surface 620 of the top substrate 618 is then mated, e.g., placed into contact with, and bonded to the planar surface 614 of the bottom substrate 612, covering and sealing the grooves and/or indentations 616 in the surface of the bottom substrate, to form the channels and/or chambers (i.e., the interior portion) of the device at the interface of these two components. The holes 624 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

Figure 7:
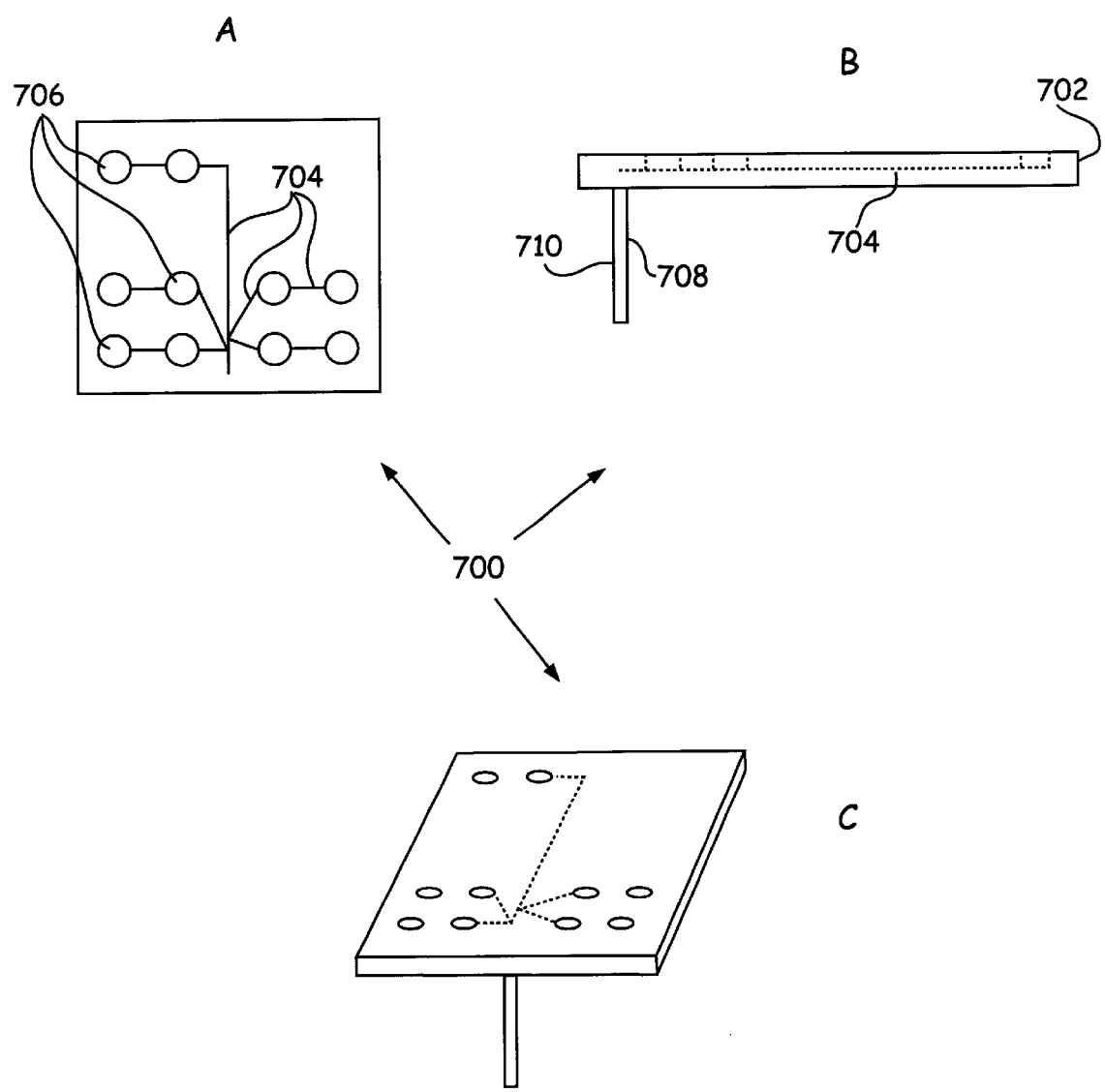
FIG. 7 is a schematic illustration of a microfluidic device incorporating an external sampling pipettor as a reaction/assay receptacle in the present invention.

As described in greater detail below, these devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. Pat. No. 5,779,868 and published International Patent Application Nos. WO 98/00705 and WO 98/00231, each of which is incorporated herein by reference in its entirety for all purposes. A schematic illustration of a microfluidic device incorporating an external sample pipettor is illustrated in FIG. 7, described below.

Briefly, a microfluidic device 700, e.g., similar to that described with reference to FIG. 6, is provided having a body structure 702 which includes a network of internal channels 704 that are connected to a series of reservoirs 706 disposed in the body structure 702. The various reservoirs are used to introduce various reagents into the channels 704 of the device. A capillary element 708 is coupled to the body structure 702, such that the channel 710 that is disposed within and runs the length of the capillary element 708 is fluidly connected to the channel network 704 in the body structure. This capillary element 708 is then used to draw up a variety of different sample or test materials, in series, for analysis within the device.

As described above, the methods and systems of the present invention typically rely upon a change in the level of fluorescence polarization of the reaction mixture as a result of the reaction of interest. As such, an appropriate detection system is typically utilized to differentiate polarized from depolarized emitted fluorescence. Generally speaking, such a detection system typically separately detects fluorescent emissions that are emitted in the same plane of the polarized excitation light, and fluorescent emissions emitted in a plane other than the plane of the excitation light.

Figure 8:
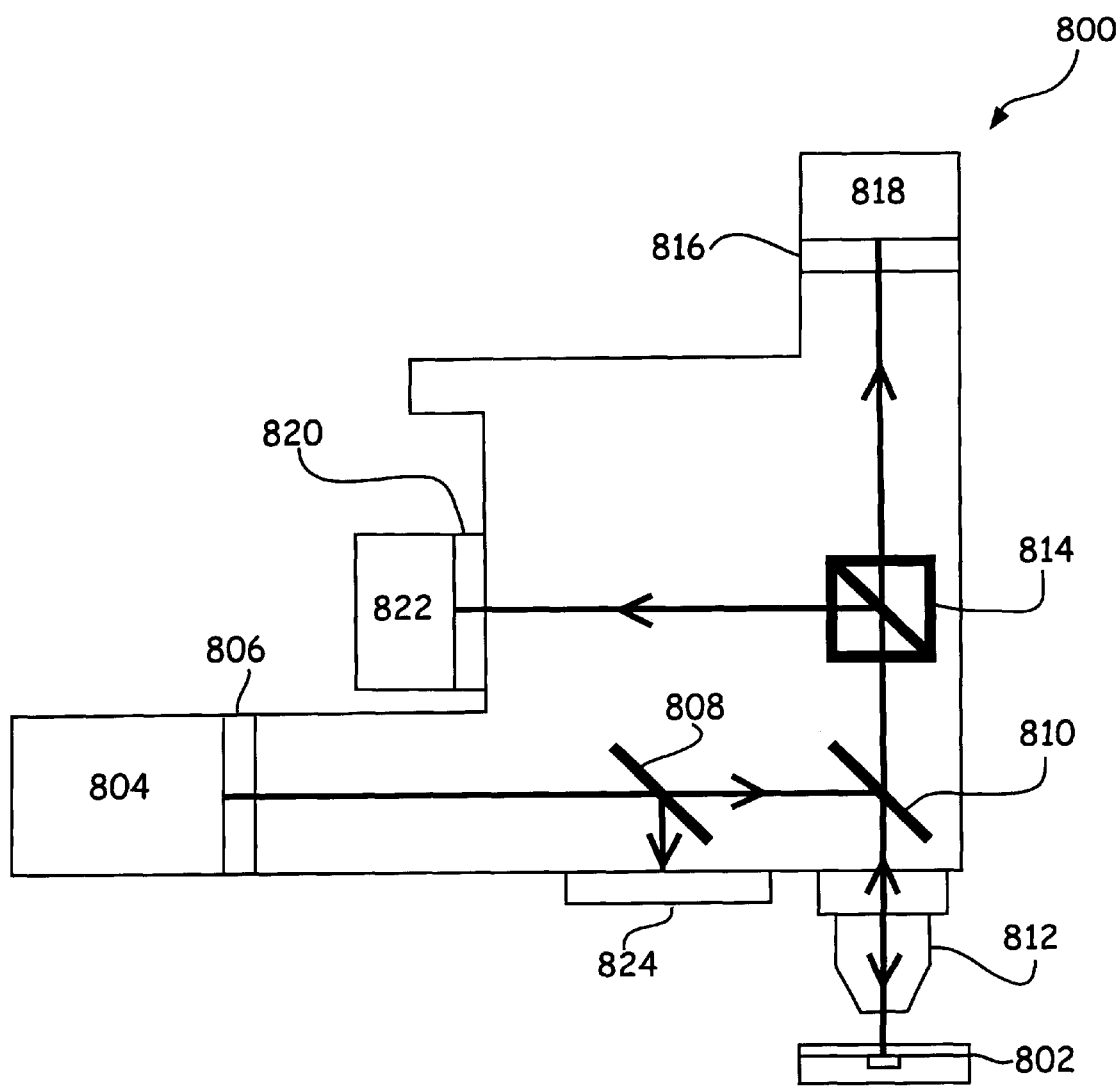
FIG. 8 is a schematic illustration of one example of an optical detection system for use with the present invention.

One example of a detection system is shown in FIG. 8. As shown, the fluorescence polarization detector includes a light source 840, which generates light at an appropriate excitation wavelength for the fluorescent compounds that are present in the assay system. Typically, coherent light sources, such as lasers, laser diodes, and the like are preferred because of the highly polarized nature of the light produced thereby. The excitation light is directed through an optional polarizing filter 806, which passes only light in one plane, e.g., polarized light. The polarized excitation light is then directed through an optical train, e.g., dichroic mirror 810 and microscope objective 812 (and optionally, reference beam splitter 808), which focuses the polarized light onto the sample receptacle (illustrated as a channel in microfluidic device 802), in which the sample to be assayed is disposed.

Fluorescence emitted from the sample is then collected, e.g., through the objective 812, and directed back through dichroic mirror 810, which passes the emitted fluorescence and reflects the reflected excitation light, thereby separating the two. The emitted fluorescence is then directed through a beam splitter 814 where one portion of the fluorescence is directed through an filter 816 that filters out fluorescence that is in the plane that is parallel to the plane of the excitation light and directs the perpendicular fluorescence onto a first light detector 818. The other portion of the fluorescence is passed through a filter 820 that filters out the fluorescence that is perpendicular to the plane of the excitation light, directing the parallel fluorescence onto a second light detector 822. In alternative aspects, beam splitter 814 is substituted with a polarizing beam splitter, e.g., a Glan prizm, obviating the need for filters 816 and 820. These detectors 818 and 822 are then typically coupled to an appropriate recorder or processor (not shown in FIG. 8) where the light signal is recorded and or processed as set out in greater detail below. Photomultiplier tubes (PMTs), are generally preferred as light detectors for the quantification of the light levels, but other light detectors are optionally used, such as photodiodes, or the like.

The detector is typically coupled to a computer or other processor, which receives the data from the light detectors, and includes appropriate programming to compare the values from each detector to determine the amount of polarization from the sample. In particular, the computer typically includes software programming which receives as input the fluorescent intensities from each of the different detectors, e.g., for parallel and perpendicular fluorescence. The fluorescence intensity is then compared for each of the detectors to yield a fluorescence polarization value. One example of such a comparison is given by the equation:

$$P=[I(\|)-I(\perp)]/[I(\|)+I(\perp)]C \quad (4)$$

as shown above, except including a correction factor (C), which corrects for polarization bias of the detecting instrument. The computer determines the fluorescence polarization value for the reaction of interest. From that polarization value and based upon the polarization values for free and bound fluorescence, the computer calculates the ratio of bound to free fluorescence. Alternatively, the polarization values pre and post reaction are compared and a polarization difference ($\Delta P$) is determined. The calculated polarization differences may then be used as absolute values, e.g., to identify potential effectors of a particular reaction, or they may be compared to polarization differences obtained in the presence of known inhibitors or enhancers of the reaction of interest, in order to quantify the level of inhibition or enhancement of the reaction of interest by a particular compound.

Figure 9:
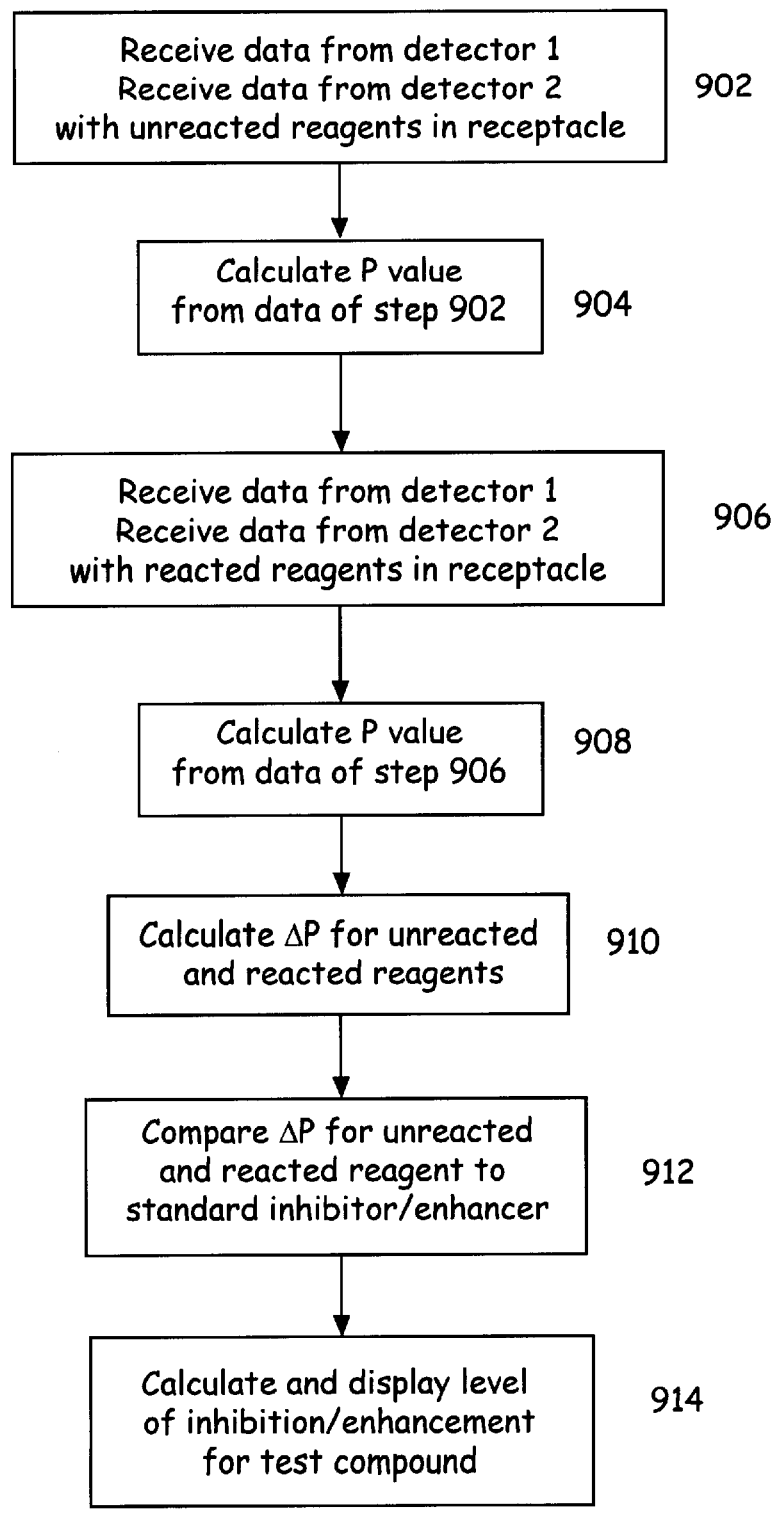
FIG. 9 is a flow chart of a software program or computer implemented process carried out by an assay system in performing the assays of the present invention.

FIG. 9 illustrates a flow-chart for the processes carried out by the computer using the above-described software programming. As shown, the programmed process begins at step 902 where the computer receives the fluorescence intensity data for the unreacted reagents in the reaction zone (e.g. in receptacle 502 of FIG. 5) from the two detectors, e.g., detectors 818 and 820 of FIG. 8. The fluorescence polarization value (P) is then calculated in step 940, e.g., according to the equations described herein. At step 906, the computer receives fluorescence intensity data for the reacted reagents from the two detectors. Again, at step 908, the P value is calculated for the reacted reagents. At step 910, the P values for the reacted and unreacted reagents are compared, e.g., one is subtracted from the other to yield a $\Delta P$ value for the reaction. At this point, the $\Delta P$ value may be displayed as a measure of the reaction, e.g., its rate or completeness. Optionally, however, the $\Delta P$ value may be compared to a standard $\Delta P$ value, i.e., from a reaction having a known rate, level of inhibition or enhancement, e.g., at step 912. Through this comparison, the computer may then interpolate or extrapolate a quantitative measure of the reaction, its level of inhibition or enhancement which quantitative measurement may then be displayed to the investigator, e.g., at step 914. As noted above, the computer may optionally include a determined polarization value for completely free and completely bound fluorescence. In that case, determination of fluorescence differences is not necessary, thus permitting the omission of several steps of the program. In that case, the computer receives the fluorescence data from the detector for the reacted mixture. The computer then merely calculates the P value for the reaction mixture and determines the ratio of bound fluorescence to free fluorescence (e.g., in accordance with equation (3), supra). The ratio is then used to quantitate the reaction.

In the case of high-throughput screening assay systems, the computer software optionally instructs the correlation of a particular screened result to a particular sample or sample acquisition location. This permits the investigator to identify the particular reagents employed in any one assay.

Figure 10A:
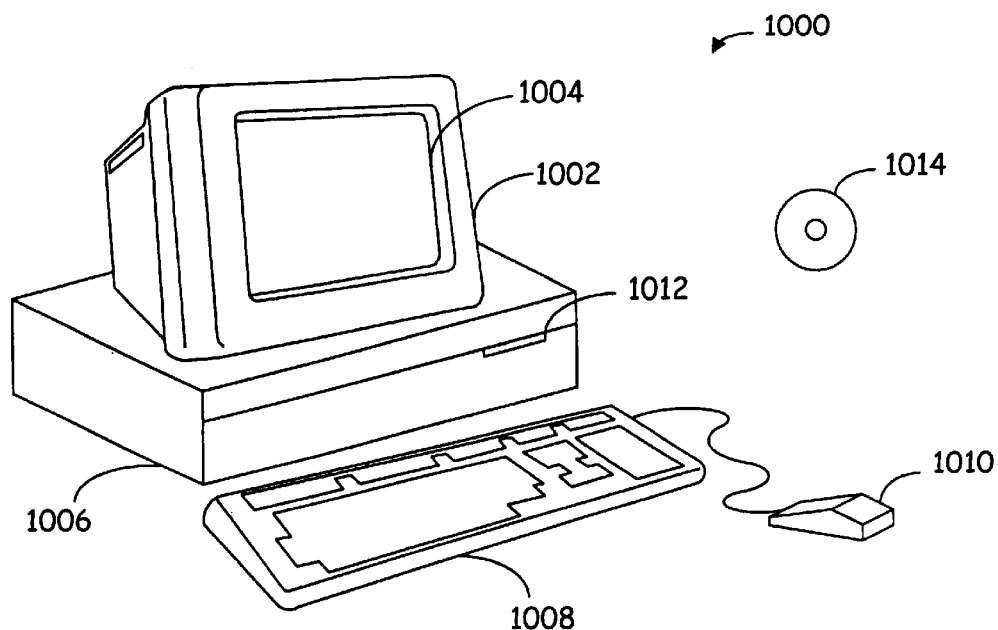
FIG. 10A illustrates an exemplary computer system that may be used to execute software for use in practicing the methods of the invention.
Figure 10B:
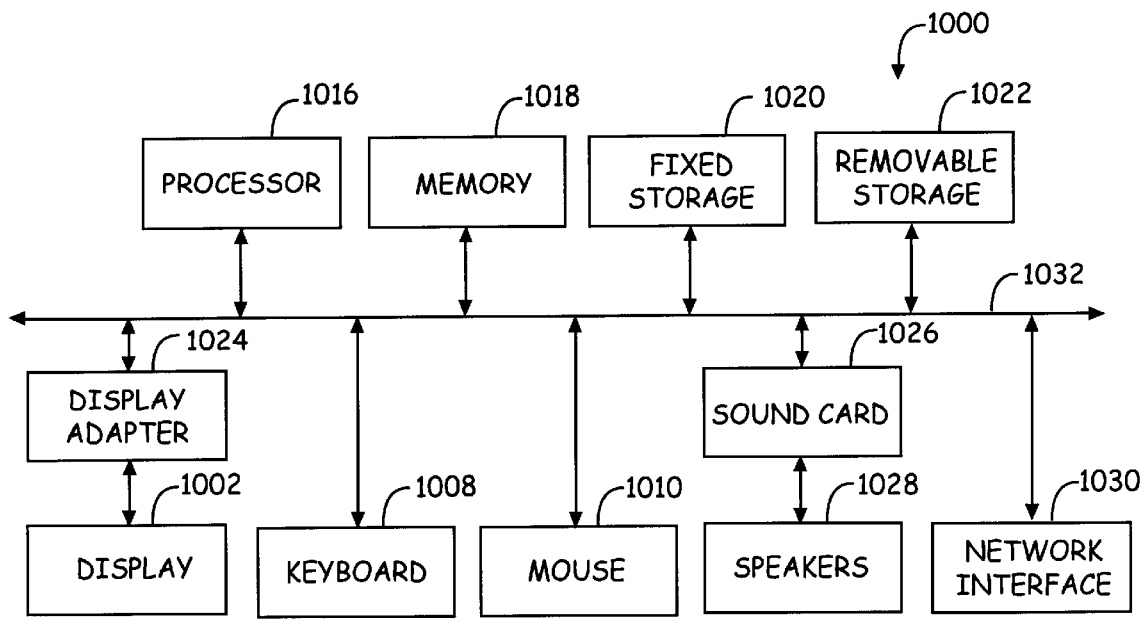
FIG. 10B illustrates a block diagram of the architecture of the computer system of FIG. 10A.

FIG. 10 schematically illustrates a computer and architecture typically used in accordance with the present invention. In particular, FIG. 10A illustrates an example of a computer system that may be used to execute software for use in practicing the methods of the invention or in conjunction with the devices and/or systems of the invention. Computer system 1000 typically includes a display 1002, screen 1040, cabinet 1006, keyboard 1008, and mouse 1010. Mouse 1010 may have one or more buttons for interacting with a graphic user interface (GUI). Cabinet 1006 typically houses a CD-ROM drive 1012, system memory and a hard drive (see FIG. 10B) which may be utilized to store and retrieve software programs incorporating computer code that implements the methods of the invention and/or controls the operation of the devices and systems of the invention, data for use with the invention, and the like. Although CD-ROM 1014 is shown as an exemplary computer readable storage medium, other computer readable storage media, including floppy disk, tape, flash memory, system memory, and hard drive(s) may be used. Additionally, a data signal embodied in a carrier wave (e.g., in a network, e.g., internet, intranet, and the like) may be the computer readable storage medium.

FIG. 10B schematically illustrates a block diagram of the computer system 1000, described above. As in FIG. 10A, computer system 1000 includes monitor or display 1002, keyboard 1008, and mouse 1010. Computer system 1000 also typically includes subsystems such as a central processor 1016, system memory 1018, fixed storage 1020 (e.g., hard drive) removable storage 1022 (e.g., CD-ROM drive) display adapter 1024, sound card 1026, speakers 1028 and network interface 1030. Other computer systems available for use with the invention may include fewer or additional subsystems. For example, another computer system optionally includes more than one processor 1014.

The system bus architecture of computer system 1000 is illustrated by arrows 1032. However, these arrows are illustrative of any interconnection scheme serving to link the subsystems. For example, a local bus could be utilized to connect the central processor to the system memory and display adapter. Computer system 1000 shown in FIG. 10A is but an example of a computer system suitable for use with the invention. Other computer architectures having different configurations of subsystems may also be utilized, including embedded systems, such as on-board processors on the controller detector instrumentation, and "internet appliance" architectures, where the system is connected to the main processor via an internet hook-up.

The computer system typically includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the optional material transport system, and/or for controlling, manipulating, storing etc., the data received from the detection system. In particular, the computer typically receives the data from the detector, interprets the data, and either provides it in one or more user understood or convenient formats, e.g., plots of raw data, calculated dose response curves, enzyme kinetics constants, and the like, or uses the data to initiate further controller instructions in accordance with the programming, e.g., controlling flow rates, applied temperatures, reagent concentrations, etc.

As described above, the present invention is optionally carried out in a microfluidic device or system. As such, it is generally desirable to provide a means or system for moving materials through, between and among the various channels, chambers and zones that are contained in such devices. A variety of material transport methods are optionally used in accordance with such microfluidic devices. For example, in one preferred aspect material movement through the channels of a device is caused by the application of pressure differentials across the channels through which material flow is desired. This may be accomplished by applying a positive pressure to one end of a channel or a negative pressure to the other end. In complex channel networks, controlled flow rates in all of the various interconnected channels may be controlled by the inclusion of valves, and the like within the device structure, e.g., to stop and start flow through a given channel. Alternatively, channel resistances may be adjusted to dictate the rate, timing and/or volume of material movement through different channels, even under a single applied pressure differential, e.g., a vacuum applied at a single channel port. Examples of such channel networks are illustrated in e.g., U.S. patent application Ser. No. 09/238,467, filed Jan. 28, 1999, and Ser. No. 09/277,367, filed Mar. 26, 1999, and U.S. Pat. No. 6,150,119 all of which are hereby incorporated herein by reference in their entirety for all purposes.

Alternately, for microfluidic applications of the present invention, controlled electrokinetic transport systems may be used. This type of electrokinetic transport is described in detail in U.S. Pat. No. 5,858,195, to Ramsey, which is incorporated herein by reference for all purposes. Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner. Although described for the purposes of illustration with respect to a four way, cross intersection, these controlled electrokinetic material transport systems can be readily adapted for more complex interconnected channel networks, e.g., arrays of interconnected parallel channels.

Figure 11:
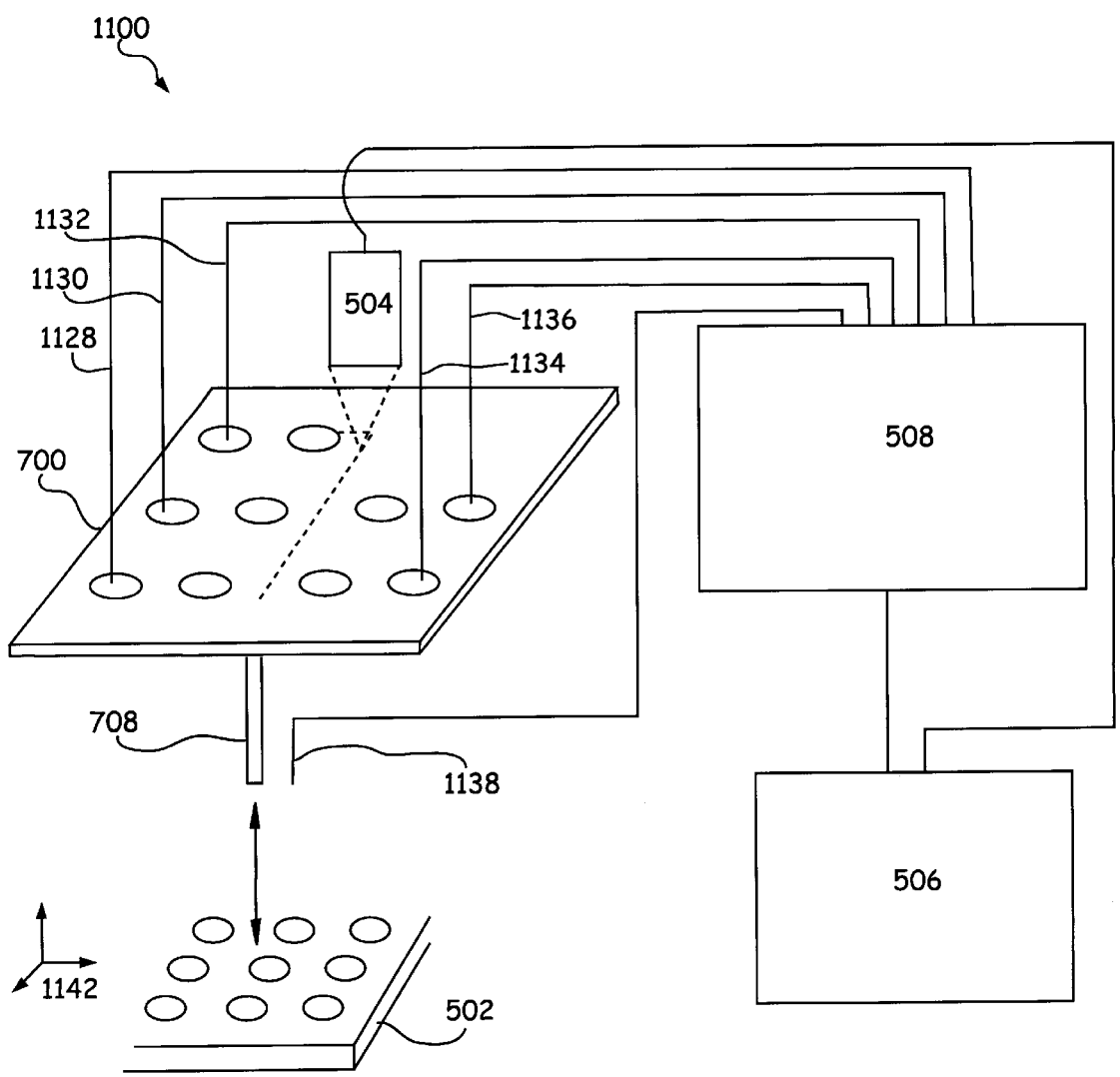
FIG. 11 illustrates the interfacing of a microfluidic device with other elements of a system for controlling material movement, detecting assay results from the microfluidic device, and analyzing those results.

An example of a system employing this type of electrokinetic transport system in a microfluidic device, e.g., as illustrated in FIG. 7, is shown in FIG. 11. As shown, the system 1100 includes a microfluidic device 700, which incorporates an integrated pipettor/capillary element 708. Each of the electrical access reservoirs 706, has a separate electrode 1128–1136 disposed therein, e.g., contacting the fluid in the reservoirs. Each of the electrodes 1128–1136 is operably coupled to an electrical controller 508 that is capable of delivering multiple different voltages and/or currents through the various electrodes. Additional electrode 1138, also operably coupled to controller 1108, is positioned so as to be placed in electrical contact with the material that is to be sampled, e.g., in multiwell plate 502, when the capillary element 708 is dipped into the material. For example, electrode 1138 may be an electrically conductive coating applied over capillary 708 and connected to an electrical lead which is operably coupled to controller 508. Alternatively, electrode 1138 may simply include an electrode wire positioned adjacent the capillary so that it will be immersed in/contacted with the sample material along with the end of the capillary element 708. Alternatively, the electrode may be associated with the source of material, as a conductive coating on the material source well or as a conductive material from which the source well was fabricated. Establishing an electric field then simply requires contacting the electrical lead with the source well material or coating. Additional materials are sampled from different wells on the multiwell plate 502, by moving one or more of the plate 502 and/or device 700 relative to each other prior to immersing the pipettor 1138 into a well. Such movement is typically accomplished by placing one or more of the device 700 or multiwell plate 502 on a translation stage, e.g., the schematically illustrated x-y-z translation stage 1142.

In still a further optional application, hybrid material transport methods and systems may be employed. Briefly, such systems often rely upon the use of electrokinetic forces to generate pressure differentials within microfluidic systems. Such hybrid systems combine the controllability of electrokinetic systems with the advantages of pressure based systems, e.g., lack of electrophoretic biasing effects. Such hybrid systems are described in, e.g., Published International Patent Application No. WO 99/16162, which is incorporated herein by reference in its entirety for all purposes.

A variety of other systems may be employed in practicing the present invention including without limitation, e.g., rotor systems, dipstick systems, spotted array systems and the like.

IV. Kits and Reagents

The reagents for carrying out the methods and assays of the present invention are optionally provided in a kit form to facilitate the application of these assays for the user. Such kits also typically include instructions for carrying out the subject assay, and may optionally include the fluid receptacle, e.g., the cuvette, multiwell plate, microfluidic device, etc. in which the reaction is to be carried out.

Typically, reagents included within the kit include the first reagent that bears the fluorescent label, as well as the polyionic compound. These reagents may be provided in vials for measuring by the user, or in pre-measured vials or ampoules which are simply combined to yield an appropriate reaction mixture. The reagents may be provided in liquid and/or lyophilized form and may optionally include appropriate buffer solutions for dilution and/or rehydration of the reagents. Typically, all of the reagents and instructions are co-packaged in a single box, pouch or the like that is ready for use.

V. Examples

Example 1

Detection of Phosphorylated Product by Fluorescent Polarization

Figure 12:
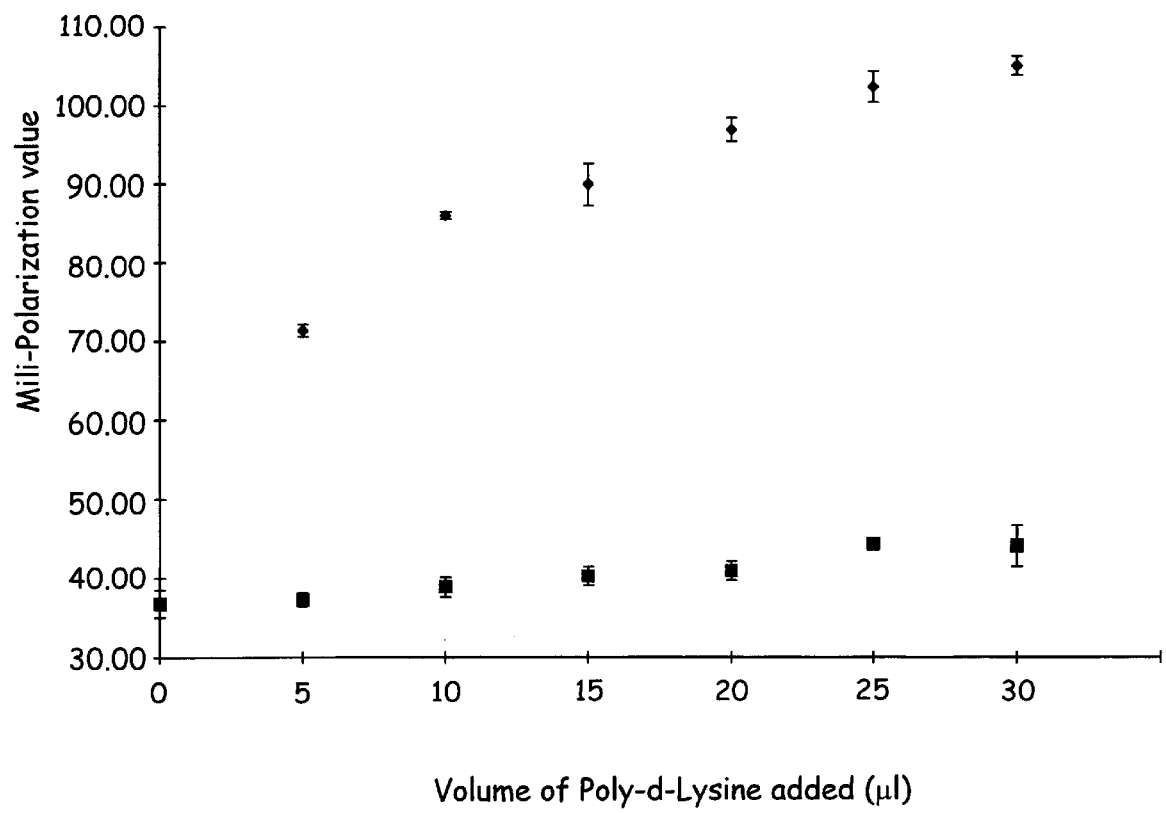
FIG. 12 is a plot of fluorescent polarization of a fluorescent phosphorylated compound in the presence of increasing amounts of a polycation.

An aliquot of a neutrally charged phosphorylatable substrate (Flourescein-QSPKKG-CONH$_2$) was incubated overnight with ATP and CDK2 (cyclin dependent kinase). The mixture was analyzed by standard capillary electrophoresis methods and showed complete conversion of substrate to product. A negative control (no enzyme) was also prepared. The two reaction mixtures were diluted in 50 mM TAPS pH 9.0 buffer (1:40). The fluorescence polarization values were measured by exciting the samples at 490 nm and measuring emitted fluorescence at 520 nm in a cuvette of a fluorimeter equipped to measure fluorescence polarization. Aliquots of a poly-D-Lysine solution and water were added (each added aliquot increased the poly-D-Lysine concentration by 6 $\mu$M). The results of the assay are illustrated in FIG. 12 which plots the fluorescent polarization of the sample versus the amount of poly-D-lysine added.

As shown, the fluorescence polarization of both substrate (square) and product (diamond) in the absence of polylysine was about 38 milli polarization units (mP). Upon addition of polylysine, the fluorescence polarization of the product increased significantly (to 72 and then to ~100 mP upon addition of a large excess of polylysine). The fluorescence polarization of the substrate only increased to about 42 mP.

Example 2

Differentiation of Product Concentrations Using Fluorescence Polarization

Additional experiments were carried out using polyhistidine in place of polylysine. In this case, the buffer used was 50 mM BisTris pH 6.5; the molecular weight of the polyhistidine used was 15800 daltons (available from Sigma Chemical, St. Louis, Mo.).

Mixtures containing varying ratios of the substrates and products of two serine/threonine kinases were prepared, CDK2 and Protein Kinase A (PKA). The CDK substrate was the same as that described for Example 1, above. The PKA substrate was: Fluor-LRRASLG where the C-terminus was either a carboxyl group or a carboxamide group. These mixtures were used as models for kinase reactions at varying degrees of substrate conversion. To these mixtures of substrate and product were added aliquots of a polyhistidine solution and water. The concentration of this aqueous stock was approximately 1.3 mM, and the final concentration was between 10 and 25 mM.

Figure 13:
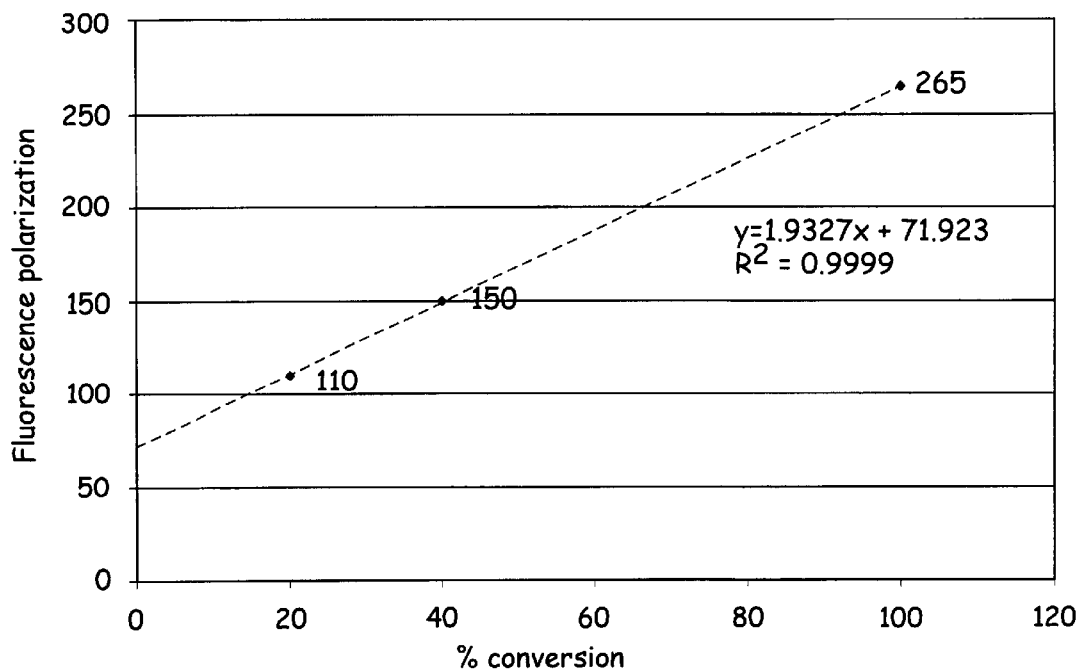
FIG. 13 is a plot of fluorescent polarization of a mixture of fluorescent phosphorylatable substrate and phosphorylated product, where the relative concentrations of substrate and product are varied, in the additional presence of a polycation.
Figure 14:
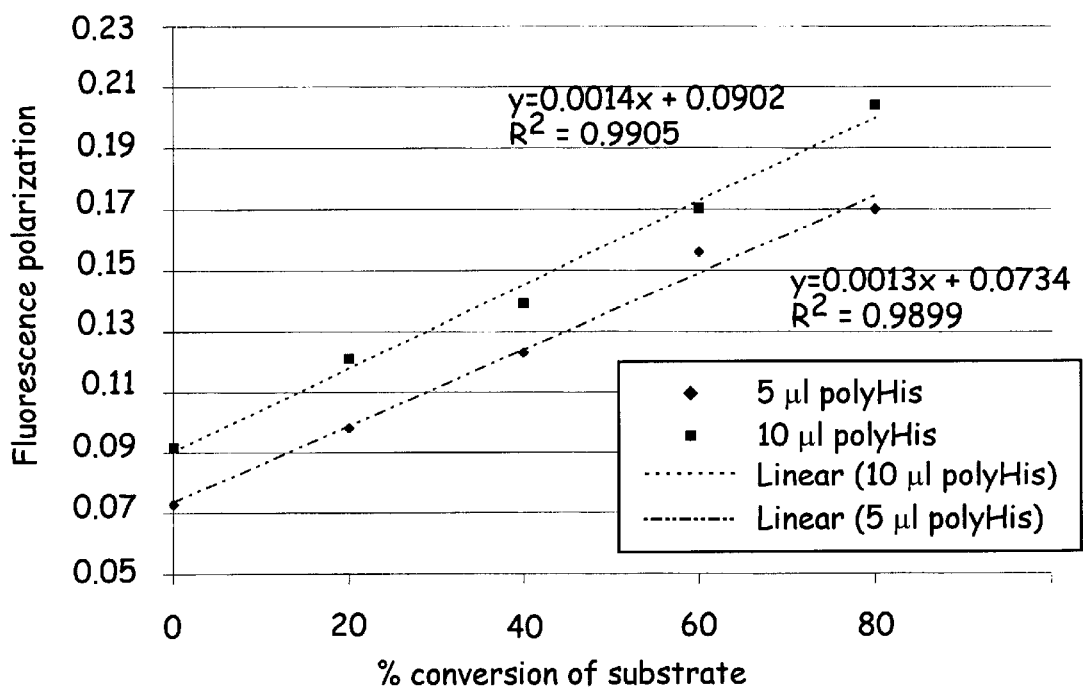
FIG. 14 is a similar plot to that shown in FIG. 13, except utilizing a different phosphorylatable substrate and phosphorylated product.

Fluorescence polarization readings were again obtained by exciting at 490 and detecting emitted fluorescence at 520 nm (both substrates were fluorescein labeled). FIGS. 13 and 14 show the results from these experiments. Briefly, FIGS. 13 and 14 are plots of fluorescence polarization in increasing concentrations of phosphorylated product as compared to substrate (denoted % conversion). In the case of FIG. 13, the substrate product are model substrate/products of a CDK2, while FIG. 14 illustrates similar data for PKA substrate/ product mixtures. As can be seen, a very good linear dependence is observed between the fluorescence polarization signal and the percent conversion. Thus, the method is well suited to follow the progress of kinase reactions and also for the screening of chemical libraries for kinase inhibitors.

Example 3

Nucleic Acid Hybridization Assay Using Fluorescence Polarization Detection

The assay methods were also employed in the detection of a nucleic acid hybridization reaction. This assay is particularly interesting due to the lack of an immobilized target sequence that was to be interrogated. In particular, the entire assay was carried out in solution.

A fluorescein-labeled peptide nucleic acid molecule 202 was used in hybridization experiments with the DNA targets 192 and 182. PNAs are generally commercially available from the Applied Biosystems Division of the Perkin-Elmer Corporation (Foster City, Calif.). The sequence of these molecules is illustrated below. In the case of the PNA molecule, the given sequence illustrates the analogous sequence of a DNA molecule. The sequences of the three molecules are as follows:

```
202: 5' F1-O-GTCAAATACTCCA          (SEQ. ID NO. 1)

192: 5' ATGGGCTGGAGTATTTGACCTAATT   (SEQ. ID NO. 2)

182: 5' CGCTGTGGATGCTGCCTGA         (SEQ. ID NO. 3)
```

DNA sequence 192 contains 13 bases (shown in bold) that are fully complementary to the PNA probe 202, whereas 182 is a non-complementary oligonucleotide.

Figure 15:
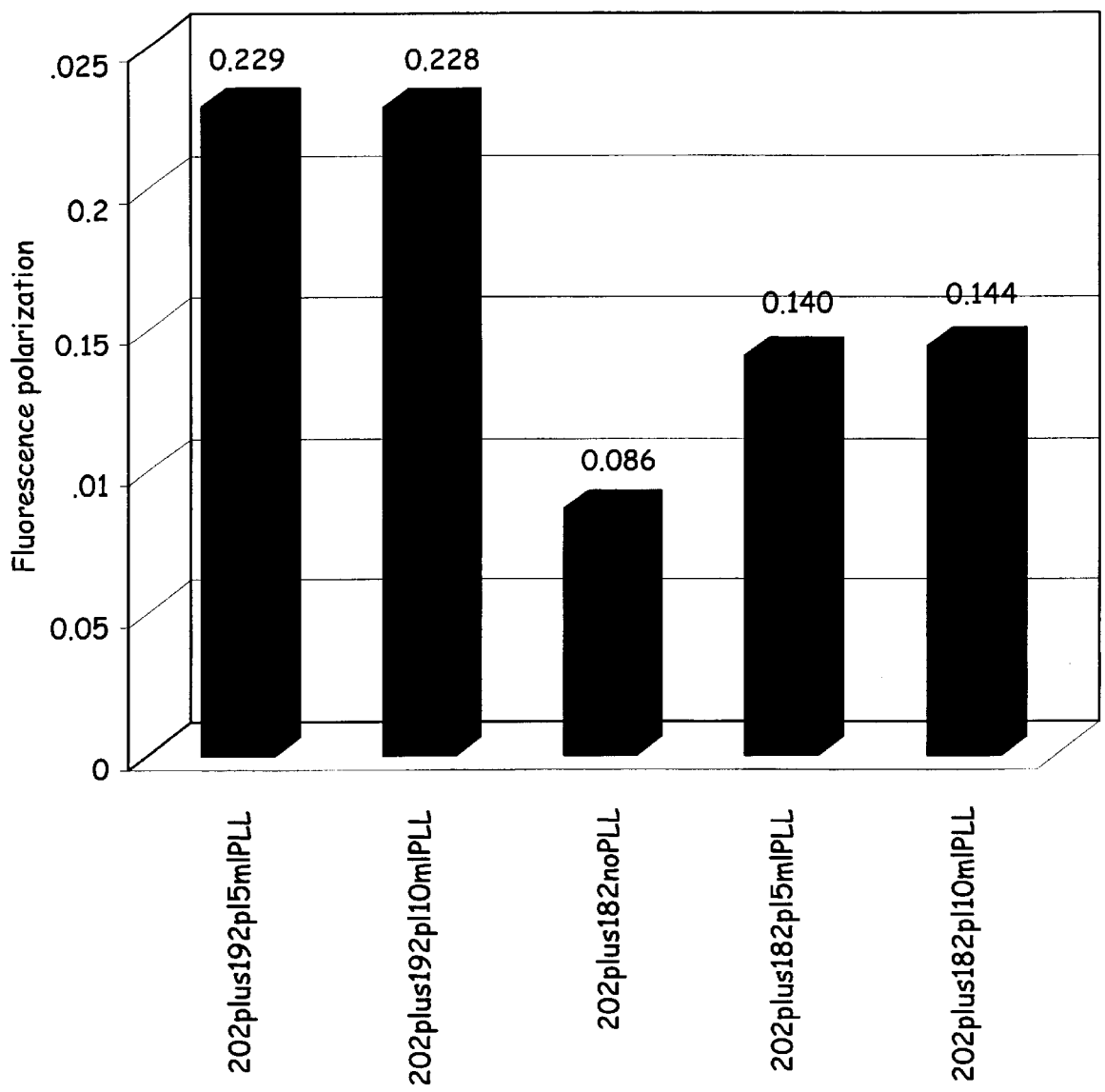
FIG. 15 is a bar graph of the fluorescent polarization level of a fluorescent PNA probe used to interrogate a non-complementary and complementary target DNA sequence, in the absence and the presence of varying levels of polycation.

A solution containing 1 $\mu$M of PNA 202 in 50 mM HEPES pH 7.5 was mixed with either 5 $\mu$M of 192 or 5 $\mu$M of 182. The mixtures were left at room temperature for about 10 min. and then placed in the cuvette of a fluorimeter equipped to measure fluorescence polarization. The measurements were carried out using 490 nm for excitation and 520 nm for detection of fluorescence emission. The fluorescence polarization values were recorded first in the absence and then in the presence of poly-L-Lysine hydrobromide, having a molecular weight of approximately 70–100 kD (Sigma Chemicals). The poly-L-Lysine was added from a stock solution in water (approx. 440 $\mu$M). The final concentrations of the poly Lysine were 4.4 and 8.8 $\mu$M. The resulting fluorescence polarization values are shown in FIG. 15.

As can be seen, a polarization value of 86 mP was obtained for the mixture containing 202 and the non-complementary 182. This increased to 140 mP in the presence of poly-L-Lysine. In contrast, the 202 hybrid with the complementary 192 sequence showed a polarization value of about 100 mP in the absence (not shown in FIG. 15) and 229 mP in the presence of poly-L-Lysine. These results demonstrate that fluorescence polarization in the presence of poly-L-Lysine can be used to detect the formation of specific PNA/DNA hybrids in solution. Such assays are readily employed in detection of the presence or absence of a particular sequence within a sample, e.g., in sequencing by hybridization, sequence checking, screening for sequence variants, e.g., polymorphisms, i.e., SNPs, STRs, and the like.

Example 4

Detection of Single Nucleotide Substitution

The assay methods were employed to detect differential hybridization of a nucleic acid probe to a perfectly complementary target sequence and a target sequence incorporating a single base variation, e.g., a single nucleotide polymorphism (SNP). In particular, a fluoresceinated PNA probe having a sequence complementary to a subsequence of a target sequence was used to probe the target including the subsequence and a target in which an interior base of the subsequence was substituted for a different base.

The 5' to 3' sequences of the PNA probe (PNA 7637)(SEQ ID NO: 4), the target DNA sequence (DNA 244)(SEQ ID NO: 5) and single base mismatch target DNA sequence (DNA 245)(SEQ ID NO 6) were as follows:

```
PNA 7637:  Fluorescein-CCTGTAGCA         (SEQ ID NO:4)

DNA 244:   TTGTTGCCAATGCTACAGGCATCGT
           (SEQ ID NO:5)

DNA 245:   TTGTTGCCAATGCTGCAGGCATCGT    NO;#)
           (SEQ ID NO:6)
```

The subsequence of the DNA targets complementary to the PNA probe are in bold. The position of the SNP is underlined.

Figure 16:
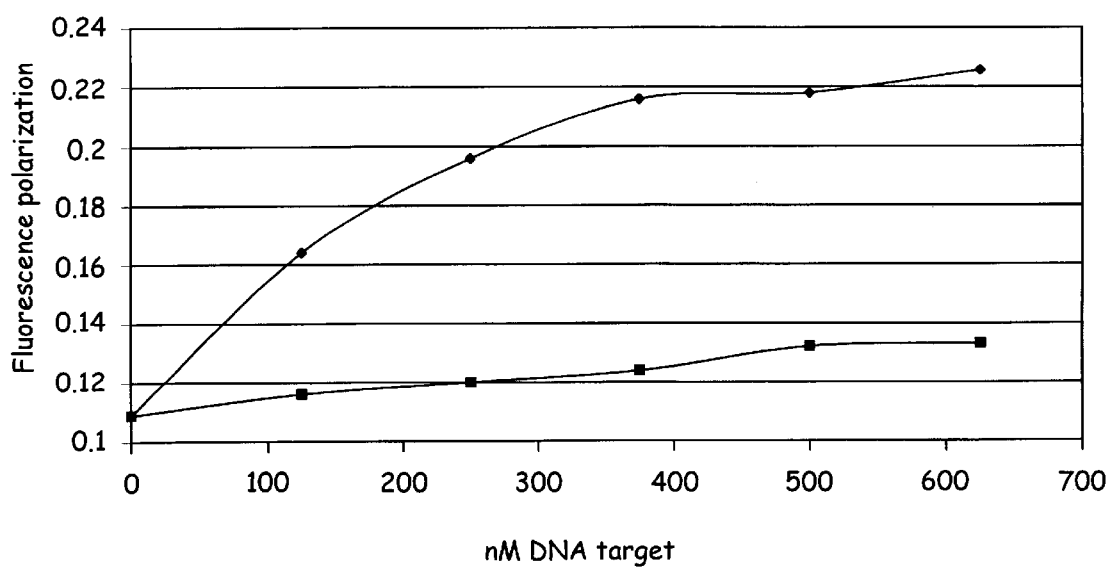
FIG. 16 is a plot of fluorescent polarization of a mixture of a target nucleic acid sequence and a perfectly complementary fluorescent PNA probe (upper line, diamonds) and a mixture of a target sequence that is complementary but for a single base mismatch with a fluorescent PNA probe (lower line, squares).

The PNA probe 7637 was used at a final concentration of 250 nM, in a reaction volume of 400 $\mu$l. The buffer used was 50 mM HEPES pH 7.5, 100 mM NaCl. The solution also contained poly-L-Lysine at about 3 $\mu$M. One $\mu$l aliquots of the DNA targets 244 and 245 were added iteratively to the PNA solution and the fluorescence polarization (excitation 490, emission 520 nm) was recorded after the addition of each aliquot. The data from this experiment is illustrated in FIG. 16. The perfectly complementary target/probe mixture (diamonds) showed substantially higher levels of fluorescence polarization, than the single base mismatched mixture (squares), indicating that a higher level of hybridization had occurred. As can also be seen, hybridization plateaued at approximately a 1 M excess of target sequence in the perfectly complementary example.

Unless otherwise specifically noted, all concentration values provided herein refer to the concentration of a given component as that component was added to a mixture or solution independent of any conversion, dissociation, reaction of that component to a alter the component or transform that component into one or more different species once added to the mixture or solution. The method steps described herein are generally performable in any order unless an order is specifically provided or a required order is clear from the context of the recited steps. Typically, the recited orders of steps reflects one preferred order.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of detecting a reaction, comprising:
providing a first mixture which comprises a first reagent having a fluorescent label;
introducing a second reagent into the first mixture to produce a second mixture, the second reagent reacting with the first reagent to produce a fluorescently labeled product having a substantially different charge than the first reagent;
introducing a polyionic polymer into at least one of the first and second mixtures; and
comparing a fluorescent polarization in the second mixture relative to the first mixture.

2. The method of claim 1, wherein the polyionic polymer associates with the product.

3. The method of claim 1, wherein the polyionic polymer associates with the first reagent.

4. The method of claim 1, wherein the polyionic polymer bears a charge that is opposite to a charge of the charged product.

5. The method of claim 1, wherein the polyionic polymer is a polycation.

6. The method of claim 5, wherein the polycation is a polyamino acid.

7. The method of claim 6, wherein the polyamino acid comprises a protein that associates with one of the fluorescent first reagent or product in a charge dependent manner.

8. The method of claim 6, wherein the polyamino acid is polylysine, polyhistidine, polyarginine, or copolymers thereof.

9. The method of claim 1, wherein the first reagent comprises an uncharged nucleic acid analog, and the second reagent comprises a nucleic acid having a nucleotide sequence complementary to a sequence of the nucleic acid analog, and the charged product comprises a hybrid of the nucleic acid analog and the nucleic acid.

10. The method of claim 9, wherein the nucleic acid analog is a peptide nucleic acid (PNA), a methyl phosphonate polymer or a cationic nucleic acid.

11. The method of claim 1, wherein the first reagent comprises a phosphorylatable compound, and the product comprises a phosphorylated first reagent.

12. The method of claim 11, wherein the second reagent comprises a kinase enzyme.

13. The method of claim 11, wherein the phosphorylatable compound comprises a peptide that comprises a phosphorylation site.

14. The method of claim 1, wherein the first reagent comprises a phosphorylated compound, and the product comprises a dephosphorylated first reagent.

15. The method of claim 14, wherein the second reagent comprises a phosphatase enzyme.

16. The method of claim 14, wherein the first reagent comprises a fluorescently labeled phosphorylated peptide.

17. The method of claim 1, wherein the first reagent is transported along a first channel, and the second reagent is introduced into the first channel to mix with the first reagent.

18. The method of claim 17, wherein the first and second reagents are introduced into the first channel via second and third channels, respectively, the second and third channels having first and second ends, and intersecting the first channel at their second ends.

19. The method of claim 18, wherein the first ends of the second and third channels are fluidly connected to first and second reservoirs, the first and second reservoirs having the first and second reagents disposed therein, respectively.

20. The method of claim 1, further comprising:
directing an excitation light at the first reagent and measuring a level of fluorescence polarization in the first reagent;
directing an excitation light at the second mixture and measuring a level of fluorescence polarization from the second mixture; and
wherein the comparing step comprises determining a first difference in the level of fluorescence polarization from the first reagent and the level of fluorescent polarization of the second mixture.

21. The method of claim 20, further comprising introducing a test compound into at least one of the first reagent and second mixture, and performing the comparing step in the presence and absence of the test compound, a decrease or increase in the first difference in the level of fluorescence polarization in the presence of the test compound relative to the difference in the absence of the test compound being indicative that the test compound is an inhibitor or enhancer of a reaction between the first and second reagents.

22. The method of claim 21, wherein the second mixture is transported along a first channel, and the test compound is introduced into the first channel.

23. The method of claim 22, wherein the first channel is fluidly connected to or is an integral portion of a capillary element, and the test compound is drawn into the capillary element from a source of the test compound.

24. The method of claim 21, wherein a plurality of different test compounds are separately introduced into separate volumes of the at least one of the first reagent and second mixture.

25. The method of claim 21, wherein the second mixture is transported along a first channel, and the plurality of test compounds are introduced into the first channel as discrete fluid regions.

26. A method of identifying the presence of a subsequence of nucleotides in a target nucleic acid, the method comprising:
contacting the target nucleic acid sequence with an uncharged, fluorescently labeled nucleic acid analog in a first reaction mixture, the nucleic acid analog being complementary to the subsequence whereby the nucleic acid analog is capable of specifically hybridizing to the subsequence to form a first hybrid;
contacting the first reaction mixture with a polyionic polymer; and
comparing a level of fluorescence polarization of the first reaction mixture in the presence of the polyionic polymer to a level of fluorescence polarization of the uncharged nucleic acid analog in the absence of the target nucleic acid sequence, an increase in the level of fluorescence polarization indicating a presence of the first hybrid.

27. The method of claim 26, wherein the nucleic acid analog is a peptide nucleic acid (PNA), a methyl phosphonate polymer, or a cationic nucleic acid.

28. The method of claim 26, wherein the polyion is a polycation.

29. The method of claim 28, wherein the polycation is a polyamino acid.

30. The method of claim 29, wherein the polyamino acid comprises a protein that associates with one of the fluorescent first reagent or product in a charge dependent manner.

31. The method of claim 29, wherein the polyamino acid is polylysine, polyhistidine, polyarginine or copolymers thereof.

32. A method of detecting the phosphorylation of a phosphorylatable compound, comprising:
providing the phosphorylatable compound with a fluorescent label;
contacting the phosphorylatable compound with a kinase enzyme in the presence of a phosphate group in a first mixture to produce a phosphorylated product;
contacting the first mixture with a polyionic polymer;
comparing a level of fluorescence polarization from the first mixture in the presence of the polyion to a level of fluorescence polarization from the phosphorylatable compound with the fluorescent label in the absence of the kinase enzyme.

33. The method of claim 32, wherein the polyionic polymer associates with the phosphorylated product.

34. The method of claim 32, wherein the polyionic polymer associates with the phosphate group.

35. The method of claim 32, wherein the polyionic polymer bears a charge that is opposite to a charge of the phosphorylated product.

36. The method of claim 32, wherein the polyionic polymer is a polycation.

37. The method of claim 36, wherein the polycation is a polyamino acid.

38. The method of claim 37, wherein the polyamino acid comprises a protein that associates with one of the phosphorylatable fluorescent compound or phosphorylated product in a charge dependent manner.

39. The method of claim 37, wherein the polyamino acid is polylysine, polyhistidine, polyarginine, or copolymers thereof.

40. A method of detecting the phosphorylation of a phosphorylatable compound, comprising:
providing the phosphorylatable compound with a fluorescent label;
contacting the phosphorylatable compound with a kinase enzyme in the presence of a phosphate group in a first mixture;
contacting the first mixture with a second reagent mixture comprising a protein having a chelating group associated therewith, and a metal ion selected from he group consisting of $Fe^{3+}$, $Ca^{2+}$, $Ni^{2+}$ and $Zn^{2+}$;
comparing a level of fluorescence polarization from the first mixture in the presence of the second mixture to a level of fluorescence polarization from the phosphorylatable compound with the fluorescent label in the absence of the kinase enzyme.

41. An assay system, comprising:
a fluid receptacle comprising:
a first reaction zone having disposed therein:
a first reagent mixture which comprises a first reagent having a fluorescent label;
a second reagent that reacts with the first reagent to produce a fluorescently labeled product having a substantially different charge than the first reagent; and
a polyionic polymer; and
a detection zone; and
a detector disposed in sensory communication with the detection zone, the detector being configured to detect a level of fluorescence polarization of reagents in the detection zone.

42. The assay system of claim 41, wherein the fluid receptacle comprises a body structure having at least a first channel disposed therein, a portion of the first channel comprising the reaction zone and a portion of the first channel comprising the detection zone.

43. The assay system of claim 42, further comprising a material transport system for transporting the first reagent, second reagent and polyionic polymer from the reaction zone portion of the first channel to the detection zone portion of the first channel.

44. The assay system of claim 43, wherein the material transport system comprises a pressure or vacuum source applied to one terminus of the first channel to push or draw fluid through from the reaction zone to the detection zone.

45. The assay system of claim 43, wherein the material transport system comprises an electrical power source operably coupled to different points in the first channel for creating an electric field across at least a portion of a length of the first channel, the electric field causing movement of material from the reaction zone to the detection zone.

46. An assay system, comprising:
a first channel disposed in a body structure, the first channel being fluidly connected to:
a source of a first reagent mixture which comprises a first reagent having a fluorescent label;
a source of a second reagent that reacts with the first reagent to produce a fluorescently labeled product having a substantially different charge than the first reagent; and
a source of a polyionic polymer;
a material transport system for introducing the first reagent, the second reagent and the polyion into the first channel; and
a detector disposed in sensory communication with the first channel, the detector being configured to detect a level of fluorescence polarization of reagents in the detection zone.

47. The assay system of claim 46, wherein the source of first reagent, the source of second reagent and the source of polyionic polymer comprise first, second and third reservoirs disposed in the body structure, respectively, the first, second and third reservoirs being fluidly connected to the first channel.

48. The assay system of claim 47, further comprising an external sampling capillary having a capillary channel disposed therethrough, the capillary channel having first and second ends, the capillary channel being fluidly connected to the first channel at the first end, and open at the second end.

49. The assay system of claim 46, further comprising a computer operably coupled to the detector, the computer being programmed to receive fluorescence polarization data from the detector, and compare a level of fluorescence polarization of the first reagent mixture to a level of fluorescence of a second reagent mixture which comprises the first reagent, the second reagent and the polyionic polymer.

50. A method for quantifying a reaction parameter comprising:

provising a first reagent mixture, which comprises a first reagent having a fluorescent label;

introducing a second reagent into the first reagent mixture to produce a second reagent mixture, the second reagent reacting with the first reagent to produce a fluorescently labeled product having a substantially different charge than the first reagent;

introducing a polyionic polymer into at least one of the first and second reagent mixtures; and initiating a computer implemented process that comprises the steps of:

determining a first level of fluorescence polarization of the first reagent mixture;

determining a second level of fluorescence polarization of the second reagent mixture;

comparing the first and second levels of fluorescent polarization; and calculating the reaction parameter.

51. The method of claim 1, wherein the first reagent mixture is provided and the second reagent is introduced into a well of a multiwell plate.

52. The method of claim 26, wherein the first reaction mixture is disposed in a well of a multiwell plate.

53. The system of claim 41, wherein the fluid receptacle comprises a well in a multiwell plate.

54. The system of claim 53, wherein the multiwell plate comprises 96 wells.

55. The system of claim 53, wherein the multiwell plate comprises 384 wells.

56. The system of claim 58, wherein the multiwell plate comprises 1536 wells.

* * * * *

UNITED STATES PATENT AND TRADEMARK OFFICE
CERTIFICATE OF CORRECTION

PATENT NO. : 6,287,774 B1
DATED : September 11, 2001
INVENTOR(S) : Nikiforov

It is certified that error appears in the above-identified patent and that said Letters Patent is hereby corrected as shown below:

<u>Title page,</u>
Please delete the title and insert the following:
-- FLUORESCENT POLARIZATION ASSAYS INVOLVING POLYIONIC POLYMERS AND SYSTEMS FOR PRACTICING SAME --.

<u>Column 31, claim 40,</u>
Line 61, please delete "he" and insert -- the --.

Signed and Sealed this

Sixteenth Day of April, 2002

*Attest:*

JAMES E. ROGAN
*Attesting Officer*  *Director of the United States Patent and Trademark Office*

SEQUENCE LISTING

<160> NUMBER OF SEQ ID NOS: 6

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Peptide
      Nucleic Acid Probe

<400> SEQUENCE: 1
gtcaaatact cca                                                          13

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:Synthetic
      Nucleic Acid

<400> SEQUENCE: 2
atgggctgga gtatttgacc taatt                                             25

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      Nucleic Acid

<400> SEQUENCE: 3
cgctgtggat gctgcctga                                                    19

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:Peptide
      Nucleic Acid Probe

<400> SEQUENCE: 4 cctgtagca                                                                9

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:Synthetic
      nucleic acids

<400> SEQUENCE: 5
ttgttgccaa tgctacaggc atcgt                                             25

<210> SEQ ID NO 6
<211> LENGTH: 25
<212> TYPE: DNA
<213> ORGANISM: Artificial Sequence -continued

```
<220> FEATURE:
<223> OTHER INFORMATION: Description of Artificial Sequence:Synthetic
      nucleic acids

<400> SEQUENCE: 6
ttgttgccaa tgctgcaggc atcgt                                          25
```